United States Patent
Nakamura

(10) Patent No.: US 11,382,604 B2
(45) Date of Patent: Jul. 12, 2022

(54) ULTRASONIC IMAGE SYSTEM WITH SYNTHESIS OF IMAGES OF DIFFERENT ULTRASONIC WAVES RECEIVED AT RESPECTIVE POSITIONS OF A PROBE

(71) Applicant: Furuno Electric Co., Ltd., Nishinomiya (JP)

(72) Inventor: Satoshi Nakamura, Nishinomiya (JP)

(73) Assignee: Furuno Electric Co., Ltd., Nishinomiya (JP)

(*) Notice: Subject to any disclaimer, the term of this patent is extended or adjusted under 35 U.S.C. 154(b) by 217 days.

(21) Appl. No.: 16/478,442

(22) PCT Filed: Dec. 12, 2017

(86) PCT No.: PCT/JP2017/044544
§ 371 (c)(1),
(2) Date: Jul. 16, 2019

(87) PCT Pub. No.: WO2018/135188
PCT Pub. Date: Jul. 26, 2018

(65) Prior Publication Data
US 2019/0365358 A1    Dec. 5, 2019

(30) Foreign Application Priority Data
Jan. 18, 2017   (JP) .............................. JP2017-006912

(51) Int. Cl.
*A61B 8/08* (2006.01)
*A61B 8/00* (2006.01)

(52) U.S. Cl.
CPC .......... *A61B 8/5253* (2013.01); *A61B 8/4254* (2013.01); *A61B 8/5207* (2013.01)

(58) Field of Classification Search
CPC .... A61B 8/5253; A61B 8/4254; A61B 8/5207
See application file for complete search history.

(56) References Cited

U.S. PATENT DOCUMENTS 8,123,691 B2 * 2/2012 Mine .................... A61B 8/0833
   600/439
8,551,004 B2 * 10/2013 Adams ................ G01S 15/8918
   600/459

(Continued)

FOREIGN PATENT DOCUMENTS

EP        1411370 A1     4/2004
JP      H05192337 A  *  8/1993
(Continued)

OTHER PUBLICATIONS

JP-4282144-B2 (Year: 2009).*
(Continued)

*Primary Examiner* — Oommen Jacob
*Assistant Examiner* — Nyrobi Celestine
(74) *Attorney, Agent, or Firm* — Alleman Hall Creasman & Tuttle LLP

(57) ABSTRACT

An ultrasonic imaging system is provided which can obtain an accurate synthesized image, even if a specimen has a surface with a large curvature. An ultrasonic imaging system may include a probe and processing circuitry. The probe may perform scan of first and second ultrasonic waves different from each other. The processing circuitry may generate a first ultrasonic image based on the first ultrasonic wave and generate a second ultrasonic image based on the second ultrasonic wave. The processing circuitry may calculate a spatial relationship based on two first ultrasonic images at two positions and two second ultrasonic images at the two positions. The processing circuitry may synthesize one of the first and second ultrasonic images at one of the two positions with the one of the first and second ultrasonic images at the other position based on the calculated relationship.

13 Claims, 14 Drawing Sheets

(56) References Cited

U.S. PATENT DOCUMENTS

| | | | | |
|---|---|---|---|---|
| 9,867,594 B2 * | 1/2018 | Hayashi | ............... | G01S 7/52047 |
| 2004/0054285 A1 | 3/2004 | Freiburger et al. | | |
| 2006/0241434 A1 * | 10/2006 | Shimazaki | ........... | A61B 8/4254 |
| | | | | 600/437 |
| 2012/0150035 A1 * | 6/2012 | Seip | ......................... | A61B 8/12 |
| | | | | 600/439 |
| 2012/0289833 A1 * | 11/2012 | Kashima | .................. | A61B 8/14 |
| | | | | 600/445 |
| 2016/0140738 A1 | 5/2016 | Asaka et al. | | |
| 2016/0367221 A1 * | 12/2016 | Igarashi | ............... | A61B 8/5253 |
| 2018/0310922 A1 * | 11/2018 | Pelissier | .............. | A61B 8/4455 |

FOREIGN PATENT DOCUMENTS

| | | | |
|---|---|---|---|
| JP | 2003038487 A | | 2/2003 |
| JP | 2003079620 A | | 3/2003 |
| JP | 4282144 B2 * | | 6/2009 |
| JP | 2011010716 A | | 1/2011 |
| JP | 4704630 B2 | | 6/2011 |
| JP | 4785105 B2 | | 10/2011 |
| JP | 2012196308 A | | 10/2012 |
| JP | 2015144623 A | | 8/2015 |
| WO | WO-2013150917 A1 * | 10/2013 | ........... A61B 8/5253 |

OTHER PUBLICATIONS

WO-2013150917-A1 (Year: 2013).*
ISA Japan Patent Office, International Search Report Issued in Application No. PCT/JP2017/044544, dated Mar. 13, 2018, WIPO, 2 pages.

* cited by examiner

ULTRASONIC IMAGE SYSTEM WITH SYNTHESIS OF IMAGES OF DIFFERENT ULTRASONIC WAVES RECEIVED AT RESPECTIVE POSITIONS OF A PROBE

CROSS REFERENCE TO RELATED APPLICATIONS

This application is a U.S. National stage of International Application No. PCT/JP2017/044544 filed on Dec. 12, 2017, which in turn claims priority to Japanese Patent Application No. 2017-006912 filed on Jan. 18, 2017, the entire disclosure of each of which is hereby incorporated herein by reference for all purposes.

TECHNICAL FIELD

The present disclosure relates to an ultrasonic imaging system, an ultrasonic imaging device, and an ultrasonic imaging method, which transmit an ultrasonic wave into a specimen, such as a human body and receive a reflected ultrasonic wave to image the inside of the specimen, and also relates to an image synthesizing program which causes a computer to synthesize the ultrasonic images.

BACKGROUND

There is an ultrasonic imaging device which performs an ultrasonic imaging at a plurality of positions of a specimen by moving a probe which transmits and receives an ultrasonic wave while bringing the probe in contact with the surface of the specimen, and synthesizes the plurality of obtained images to generate a panorama image. In order to perform the image synthesis accurately, it is necessary to accurately obtain a spatial relationship between respective images (an amount of translation, and a rotational angle).

Patent Document 1 discloses a device which selects, among a first image and a second image to be synthesized, two reference points from the first image, searches the second image, by pattern matching, for a point with an image pattern which suits the best with an image pattern in peripheral areas of the reference points, and calculates the spatial relationship (the amount of translation and the rotational angle) based on a mobile vector of the two reference points. Moreover, Patent Document 2 discloses a device which calculates a projection distribution in the horizontal direction and the vertical direction for each of two ultrasonic images to be synthesized, and calculates the spatial relationship by obtaining a correlation between the projection distributions.

REFERENCE DOCUMENT OF CONVENTIONAL ART

Patent Documents

Patent Document 1: JP4,704,630B2
Patent Document 2: JP4,785,105B2

DETAILED DESCRIPTION

If the width of the probe is large, a large imaging range corresponding to the probe width can be secured. However, when carrying out the ultrasonic imaging of a part of the human body with a comparatively large curvature, such as a leg, or an upper limb, the large-width probe causes a problem that it does not conform to the surface of the specimen. In this case, if the probe is pushed against the specimen surface or a standoff is used, it causes to the specimen to be deformed and causes a bad influence to the synthesized image. On the other hand, if the width of the probe is made smaller, the deformation problem of the specimen as described above can be solved. However, for example, in a scanning method with a small imaging range, such as a linear scan, the width of the obtained ultrasonic image becomes smaller, and therefore, it becomes difficult to accurately calculate the spatial relationship between the two images. Moreover, for example, a wide angle scanning method, such as a sector scan, can secure a larger imaging area even if the probe width is small. However, a drive frequency of the probe is low, and therefore, a resolution of the obtained ultrasonic image may be lowered. It is difficult to obtain the accurate spatial relationship from the low resolution image. If the spatial relationship between the two images cannot be obtained accurately, the accurate synthesized image cannot be obtained.

The present disclosure is made in view of the above situations, and a main purpose thereof is to provide an ultrasonic imaging system, an ultrasonic imaging device, an ultrasonic imaging method, and an image synthesizing program, which can obtain an accurate synthesized image, even if a specimen has a surface with a large curvature.

SUMMARY

In order to solve the problem described above, an ultrasonic imaging system according to one aspect of the present disclosure may include a probe, an image generator (processing circuitry), a spatial relationship calculating module (processing circuitry), and an image synthesizing module (processing circuitry). The probe may transmit first and second ultrasonic waves different from each other into a specimen through the surface of the specimen and receive the first and second ultrasonic waves reflected on the inside of the specimen. The image generator may generate a first ultrasonic image based on the first ultrasonic wave received by the probe and generate a second ultrasonic image based on the second ultrasonic wave received by the probe. The spatial relationship calculating module may calculate a spatial relationship between two different positions on the surface of the specimen based on two first ultrasonic images and two second ultrasonic images, the two first ultrasonic images being generated by the image generator based on the first ultrasonic waves received by the probe at the two positions, and the two second ultrasonic images being generated by the image generator based on the second ultrasonic waves received by the probe at the two positions. The image synthesizing module may synthesize one of the first and second ultrasonic images at one of the two positions with the one of the first and second ultrasonic images at the other position based on the relationship between the two positions calculated by the spatial relationship calculating module.

The probe may transmit the first and second ultrasonic waves by different scanning modes.

The probe may transmit the first and second ultrasonic waves at different frequencies.

Moreover, an ultrasonic imaging device according to another aspect of the present disclosure may include an image generator (processing circuitry), a spatial relationship calculating module (processing circuitry), and an image synthesizing module (processing circuitry). The image generator may, using a probe configured to transmit first and second ultrasonic waves different from each other into a specimen through the surface of the specimen and receive the first and second ultrasonic waves reflected on the inside of the specimen, generate a first ultrasonic image based on the first ultrasonic wave received by the probe and generate a second ultrasonic image based on the second ultrasonic wave received by the probe. The spatial relationship calculating module may calculate a spatial relationship between two different positions on the surface of the specimen based on two first ultrasonic images and two second ultrasonic images, the two first ultrasonic images being generated by the image generator based on the first ultrasonic waves received by the probe at the two positions, and the two second ultrasonic images being generated by the image generator based on the second ultrasonic waves received by the probe at the two positions. The image synthesizing module may synthesize one of the first and second ultrasonic images at one of the two positions with the one of the first and second ultrasonic images at the other position based on the relationship between the two positions calculated by the spatial relationship calculating module.

The image generator may generate the first ultrasonic image, and the second ultrasonic image having a narrower imaging range and higher resolution than those of the first ultrasonic image.

The image generator may generate the first and second ultrasonic images for one frame based on the first and second ultrasonic waves resulted from the probe continuously transmitting the first and second ultrasonic waves into the specimen while moving along the surface of the specimen and continuously receiving the first and second ultrasonic waves reflected on the inside of the specimen. The spatial relationship calculating module may calculate the relationship between the two positions based on two of the first ultrasonic images and two of the second ultrasonic images in each of continuous first and second frames.

The spatial relationship calculating module may calculate the relationship between the two positions including a distance between the two positions in two directions intersecting each other.

The spatial relationship calculating module may calculate the relationship between the two positions further including a rotational angle of the probe in a plane extending in the two directions.

The ultrasonic imaging device may further include a rotational angle calculating module (processing circuitry) configured to calculate the rotational angle of the probe at each of the two positions in the plane extending in the two directions, based on an angle detected at each of the two positions by a sensor configured to detect a direction of the probe in which the probe faces. The image synthesizing module may synthesize one of the first and second ultrasonic images at one of the two positions with the one of the first and second ultrasonic images at the other position, based on the distance calculated by the spatial relationship calculating module and the rotational angle calculated by the rotational angle calculating module.

The spatial relationship calculating module may include a spatial relationship estimating module (processing circuitry) configured to calculate a first relational amount that is an estimation value of the relationship between the two positions, based on the two first ultrasonic images, and a spatial relationship correcting module (processing circuitry) configured to calculate a second relational amount resulted from correcting the first relational amount calculated by the spatial relationship estimating module, based on the two second ultrasonic images. The image synthesizing module may synthesize one of the first and second ultrasonic images at one of the two positions with the one of the first and second ultrasonic images at the other position, based on the second relational amount calculated by the spatial relationship correcting module.

The spatial relationship estimating module may calculate the first relational amount including the distance between the two positions in two directions intersecting each other. The spatial relationship correcting module may calculate the second relational amount resulted from correcting the distance calculated by the spatial relationship estimating module.

The spatial relationship estimating module may calculate the first relational amount by extracting a feature point of each of the two first ultrasonic images and determining a correlation of the feature points between the two first ultrasonic images.

The spatial relationship correcting module may calculate the second relational amount based on a correlation of a luminance distribution of the two second ultrasonic images.

The image generator may generate the first ultrasonic image that is a sector scan image based on the first ultrasonic wave received when the probe transmits the first ultrasonic wave in a fan shape into the specimen, and generate the second ultrasonic image that is a linear scan image based on the second ultrasonic wave received when the probe transmits the second ultrasonic wave in a belt-shaped range into the specimen.

Further, an ultrasonic imaging method according to still another aspect of the present disclosure is an ultrasonic imaging method which may include the steps of causing a probe configured to transmit and receive ultrasonic waves, to transmit first and second ultrasonic waves different from each other into a specimen at two different positions of the surface of the specimen and receive the first and second ultrasonic waves reflected on the inside of the specimen at each of the two positions, generating two first ultrasonic images based on the first ultrasonic waves received by the probe at the two positions, generating two second ultrasonic images based on the second ultrasonic waves received by the probe at the two positions, calculating a spatial relationship between the two positions based on the two first ultrasonic images and the two second ultrasonic images, and synthesizing one of the first and second ultrasonic images at one of the two positions with the one of the first and second ultrasonic images at the other position based on the calculated relationship between the two positions.

Furthermore, an image synthesizing program according to still another aspect of the present disclosure is an image synthesizing program causing a computer to execute processing of synthesizing a plurality of ultrasonic images obtained by imaging inside of a specimen. The program may cause the computer to execute the steps of calculating, on the basis of two first ultrasonic images generated based on first ultrasonic waves received by a probe at two different positions of the surface of the specimen and two second ultrasonic images generated based on second ultrasonic waves received by the probe at the two positions, a spatial relationship between the two positions, the probe transmitting the first and second ultrasonic waves different from each other into the specimen through the surface of the specimen and receiving the first and second ultrasonic waves reflected on the inside of the specimen, and synthesizing one of the first and second ultrasonic images at one of the two positions with the one of the first and second ultrasonic images at the other position based on the calculated relationship between the two positions.

Effect of the Disclosure

According to the present disclosure, the accurate synthesized image can be obtained, even if the specimen has the surface with the large curvature.

Hereinafter, desirable embodiments of the present disclosure will be described with reference to the drawings.

Embodiment 1

In this embodiment, a sector scan and a linear scan may alternately be repeated by a probe. Based on two sector scan images obtained by twice sector scans at two positions, a first relational amount (an amount of translation and a rotational angle) which is an estimated value of a relationship between the two positions may be calculated. A second relational amount, which is obtained by correcting the first relational amount, may be calculated based on two linear scan images obtained by twice linear scans performed immediately after each of the twice sector scans. The sector scan image and the linear scan image may be synthesized based on the second relational amount.

<Configuration of Ultrasonic Imaging System>

Figure 1:
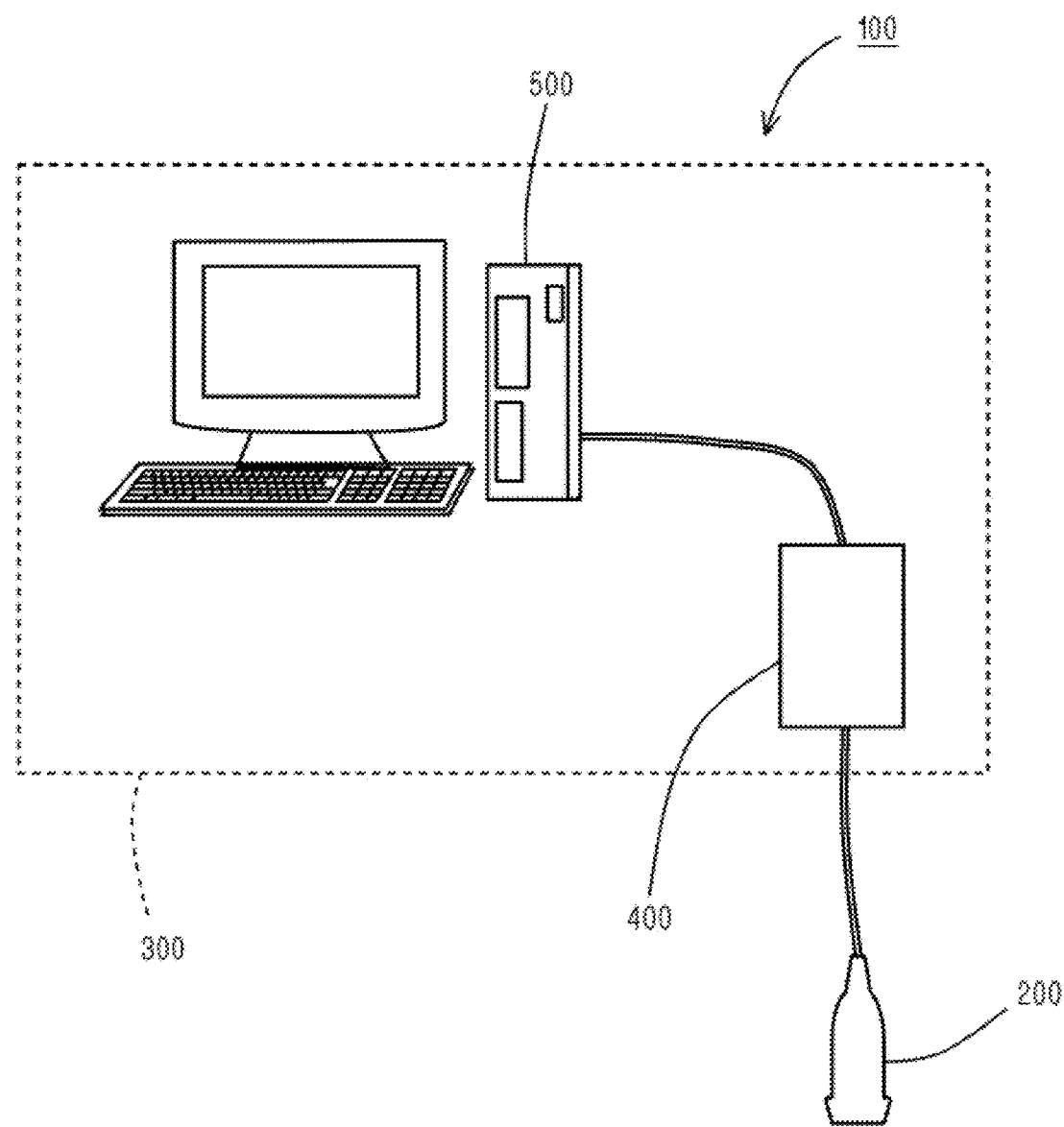
FIG. 1 is a schematic view illustrating a configuration of an ultrasonic imaging system according to Embodiment 1.

FIG. 1 is a schematic view illustrating a configuration of an ultrasonic imaging system according to this embodiment. As illustrated in FIG. 1, an ultrasonic imaging system 100 may include a probe 200 and an ultrasonic imaging device 300. Moreover, the ultrasonic imaging device 300 may include a control device 400 and an image synthesizing device 500. The probe 200 may be connected with the image synthesizing device 500 through the control device 400.

Figure 2:
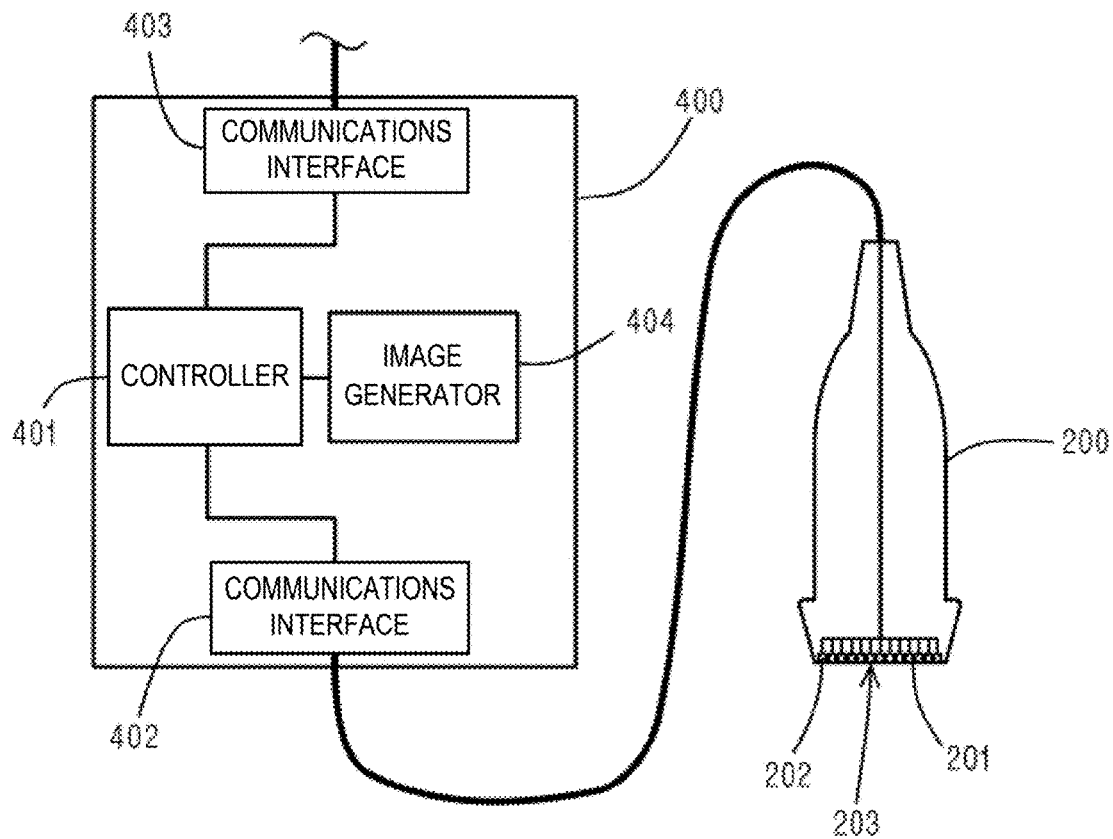
FIG. 2 is a schematic view illustrating a configuration of a probe and a control device of the ultrasonic imaging system according to Embodiment 1.

FIG. 2 is a schematic view illustrating a configuration of the probe 200 and the control device 400. The probe 200 may have such a shape that an operator is grippable. An ultrasonic transmission/reception surface 201 may be provided to a tip-end side of the probe 200. On the other hand, a cable may extend from a base end of the probe 200 and may be connected to the control device 400.

On the ultrasonic transmission/reception surface 201, an ultrasonic array sensor 203 may be comprised of a plurality of linearly-arrayed ultrasonic transducers 202. The ultrasonic array sensor 203 may be connected to the control device 400, transmit an ultrasonic wave in response to a control signal given from the control device 400, and receive a reflected ultrasonic wave. From the ultrasonic array sensor 203, an electrical signal indicative of the received ultrasonic wave may be outputted to the control device 400.

The control device 400 may include a controller 401 comprised of a CPU and a memory, communications interfaces 402 and 403, and an image generator 404. The communications interface 402 may be connected with the probe 200 and communicate with the probe 200. The communications interface 403 may be connected with the image synthesizing device 500, and communicate with the image synthesizing device 500. The image generator 404 may generate an image based on the electrical signal outputted from the ultrasonic array sensor 203.

The controller 401 may control the communications interfaces 402 and 403 and the image generator 404 according to an instruction given from the image synthesizing device 500. Moreover, the controller 401 may transmit the control signal to the probe 200 through the communications interface 402 according to an instruction given from the image synthesizing device 500. By the control of the controller 401, the probe 200 may alternately operate a sector scan mode and a linear scan mode. Thus, the control device 400 may be controlled by the image synthesizing device 500.

Figure 3A:
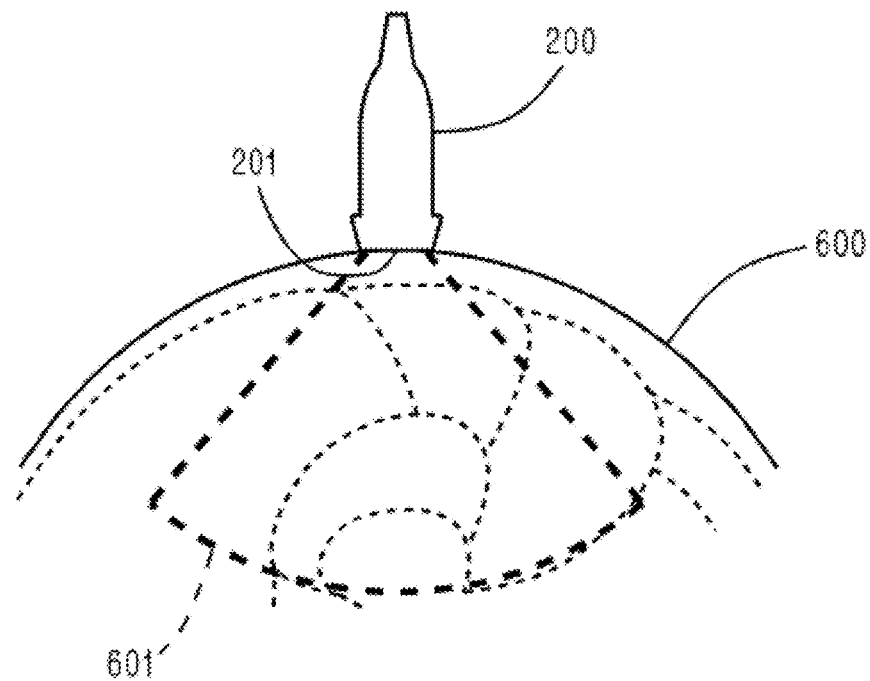
FIG. 3A is a conceptual view illustrating operation of the probe when imaging a cross-section of a thigh in a sector scan mode.
Figure 4A:
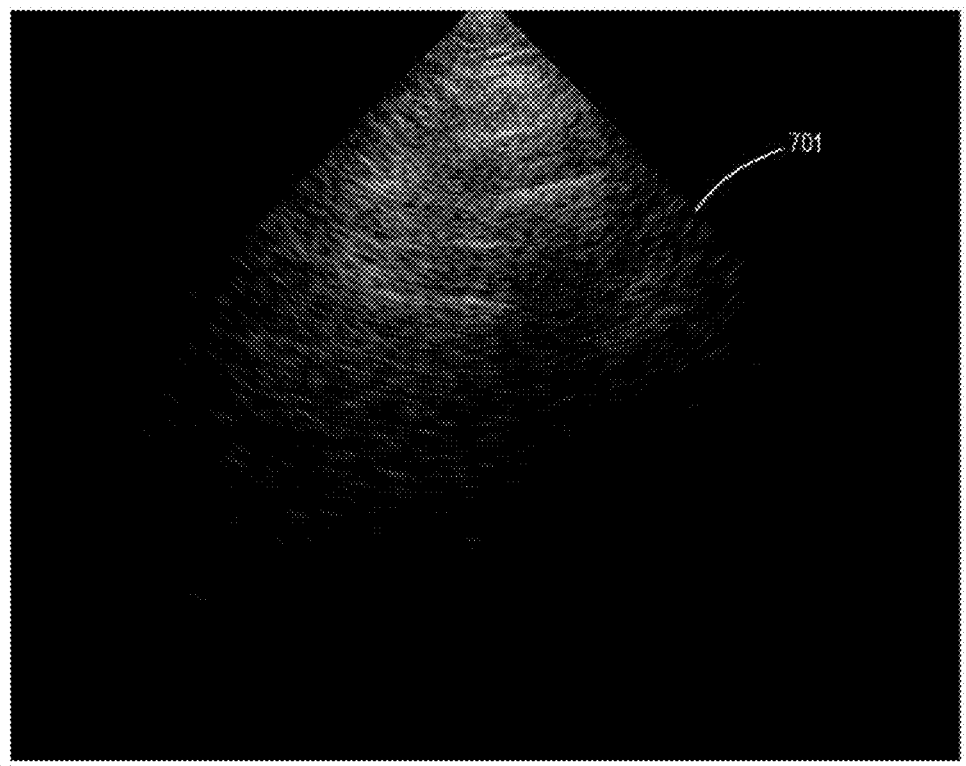
FIG. 4A is a view illustrating one example of a first ultrasonic image.

The operating mode of the probe 200 is described. The probe 200 can operate in the sector scan mode. FIG. 3A is a conceptual view illustrating operation of the probe 200 when imaging a cross-section of a thigh 600 in the sector scan mode. In the sector scan mode, the control device 400 may cause each ultrasonic transducer 202 to vibrate with a given phase difference to form an ultrasonic beam transmitted from the probe 200 into a sector shape. A drive frequency of the ultrasonic array sensor 203 in the sector scan mode is about 3 MHz, for example. Hereinafter, the ultrasonic wave transmitted from the probe 200 in the sector scan mode may be referred to as the "first ultrasonic wave." The first ultrasonic wave may be reflected on the inside of the thigh 600 which is a specimen, and a reflection wave may be received by the ultrasonic array sensor 203. Here, the electrical signal outputted from the ultrasonic array sensor 203 may be given to the image generator 404, and the image generator 404 may convert the electrical signal into an ultrasonic image in the sector scan mode (hereinafter, referred to as the "first ultrasonic image"). FIG. 4A is a view illustrating one example of the first ultrasonic image. As illustrated in FIG. 4A, the first ultrasonic image 701 may be a cross-sectional image indicating a sector-shaped imaging range 601 (see FIG. 3A).

Figure 3B:
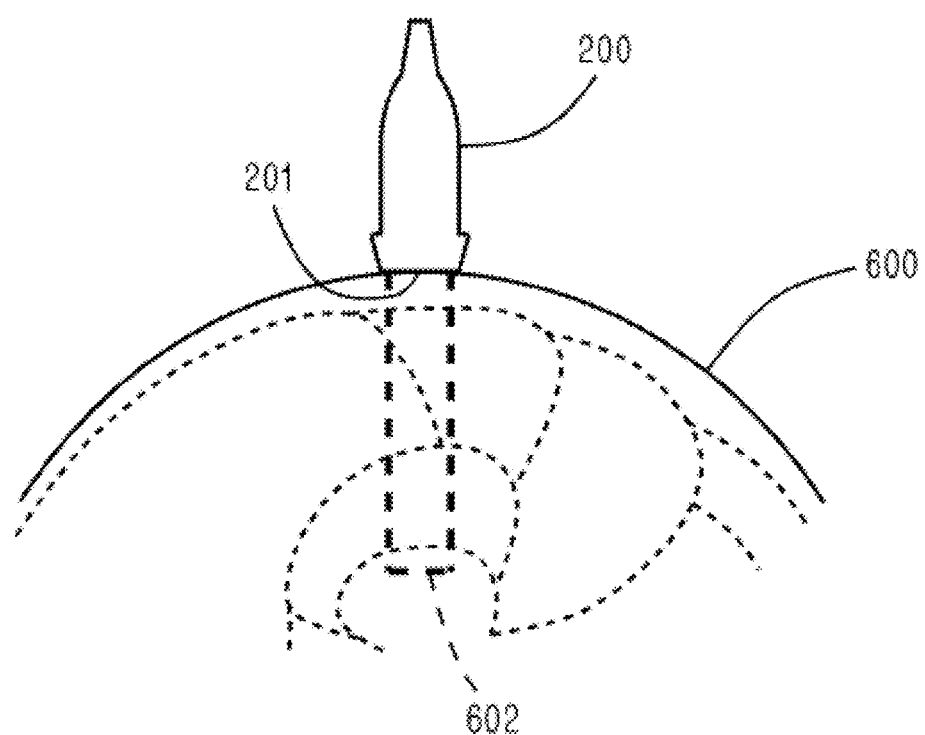
FIG. 3B is a conceptual view illustrating operation of the probe when imaging the cross-section of the thigh in a linear scan mode.
Figure 4B:
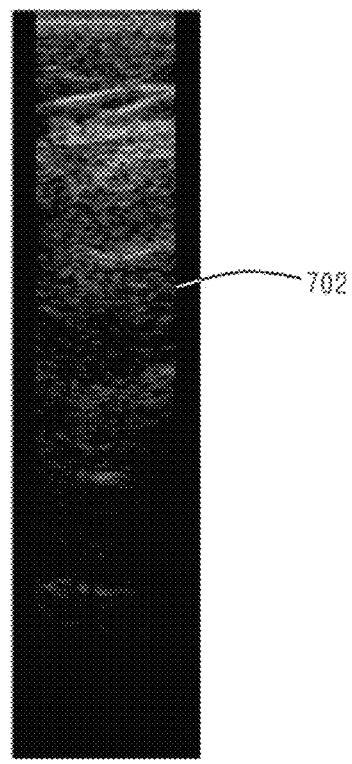
FIG. 4B is a view illustrating one example of a second ultrasonic image.

Moreover, the probe 200 can also operate in the linear scan mode. FIG. 3B is a conceptual view illustrating operation of the probe 200 when imaging the cross-section of the thigh 600 in the linear scan mode. In the linear scan mode, the control device 400 may cause each ultrasonic transducer 202 to vibrate with a synchronized phase to form an ultrasonic beam transmitted from the probe 200 into a belt shape extending in a direction perpendicular to the ultrasonic transmission/reception surface 201. A drive frequency of the ultrasonic array sensor 203 in the linear scan mode is about 6 MHz, for example. Hereinafter, the ultrasonic wave transmitted from the probe 200 in the linear scan mode may be referred to as the "second ultrasonic wave." The second ultrasonic wave may be reflected on the inside of the thigh 600 which is the specimen, and the reflection wave may be received by the ultrasonic array sensor 203. Here, the electrical signal outputted from the ultrasonic array sensor 203 may be given to the image generator 404, and the image generator 404 may convert the electrical signal into an ultrasonic image in the linear scan mode (hereinafter, referred to as the "second ultrasonic image"). FIG. 4B is a view illustrating one example of the second ultrasonic image. As illustrated in FIG. 4B, the second ultrasonic image 702 may be a cross-sectional image indicating a belt-shaped imaging range 602 (see FIG. 3B).

As described above, the belt-shaped imaging range 602 in the linear scan mode may only have a width about the same as the length of the ultrasonic array sensor 203 (i.e., a probe width). On the other hand, the imaging range 601 in the sector scan mode may be spread in a fan shape from the ultrasonic array sensor 203 (see FIGS. 3A and 3B). Thus, the imaging range 602 of the second ultrasonic image 702 may be smaller than the imaging range 601 of the first ultrasonic image 701. Moreover, in the sector scan, the scan of the ultrasonic beam may be performed at a comparatively low drive frequency (the center frequency is 2 to 7 MHz), and the range of the ultrasonic wave may be longer than that of the linear scan so that the ultrasonic wave reaches a deeper part. In the linear scan, the scan of the ultrasonic beam may be performed at a comparatively high drive frequency (the center frequency is 2.5 to 12 MHz) and the range of the ultrasonic wave may be shorter than that of the sector scan. That is, the imaging range 601 of the sector scan may be larger also in the depth direction than the imaging range 602 of the linear scan. On the other hand, regarding the resolution of the image, since the drive frequency of the ultrasonic array sensor 203 in the linear scan mode is larger than the drive frequency in the sector scan mode, the resolution of the second ultrasonic image 702 may be higher than the resolution of the first ultrasonic image 701.

Figure 5:
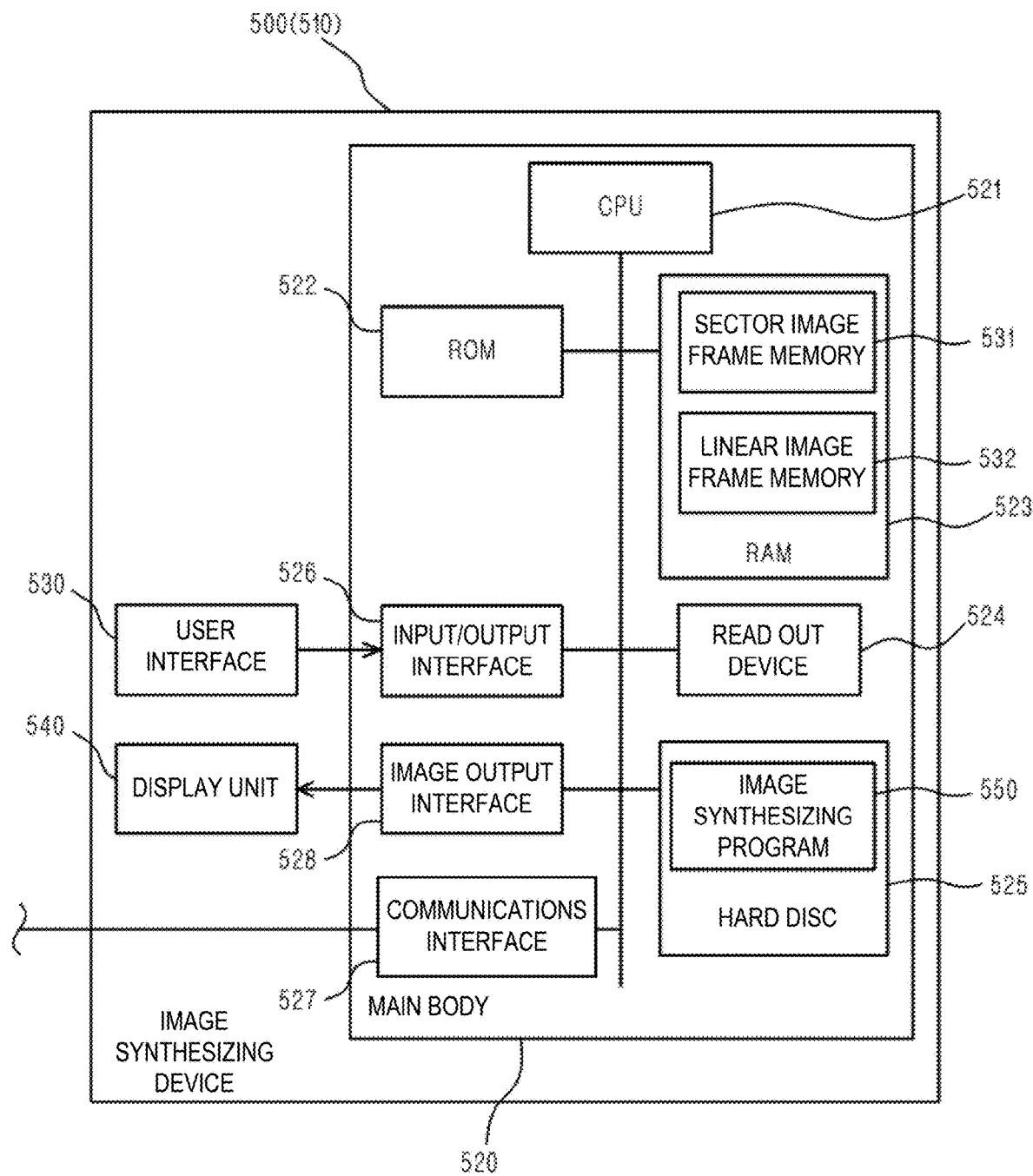
FIG. 5 is a block diagram illustrating a configuration of an image synthesizing device.

Next, a configuration of the image synthesizing device 500 is described. FIG. 5 is a block diagram illustrating a configuration of the image synthesizing device 500. The image synthesizing device 500 may be implemented by a computer 510. As illustrated in FIG. 5, the computer 510 may include a computer body 520, a user interface 530, and a display unit 540. The computer body 520 may include a CPU 521, a ROM 522, a RAM 523, a read-out device 524, a hard disk drive 525, an input/output (I/O) interface 526, a communications interface 527, and an image output interface 528. The CPU 521, the ROM 522, the RAM 523, the read-out device 524, the hard disk drive 525, the input/output interface 526, the communications interface 527, and the image output interface 528 may be connected via a bus.

The CPU 521 may execute a computer program loaded to the RAM 523. By the CPU 521 executing an image synthesizing program 550 which is a computer program for ultrasonic imaging, the computer 510 may function as the image synthesizing device 500, and it may be combined with the control device 400 to function as the ultrasonic imaging device 300.

The computer program executed by the CPU 521, and data used for the program may be recorded on the ROM 522. The RAM 523 may be used for reading out the image synthesizing program 550 recorded on the hard disk drive 525. Moreover, the RAM 523 may be used as a workspace for the CPU 521, when the CPU 521 executes the computer program.

The various computer programs executed by the CPU 521, such as an operating system and an application program, and data used for the execution of the computer programs may be installed in the hard disk drive 525. The image synthesizing program 550 may be also installed in the hard disk drive 525.

The user interface 530 comprised of, for example, a keyboard and a mouse may be connected to the input/output interface 526.

The control device 400 may be connected to the communications interface 527, and the communications interface 527 may transmit the control signal from the CPU 521 to the control device 400, and receive the first and second ultrasonic images 701 and 702 from the control device 400. Moreover, the RAM 523 may include a sector image frame memory 531 and a linear image frame memory 532. The received first ultrasonic image 701 may be stored in the sector image frame memory 531, and the second ultrasonic image 702 may be stored in the linear image frame memory 532.

The image output interface 528 may be connected to the display unit 540 comprised of, for example, an LCD or a CRT, and output to the display unit 540 an image signal according to the image data given from the CPU 521. The display unit 540 may display an image (screen) according to the inputted image signal.

<Operation of Ultrasonic Imaging System>

Figure 6:
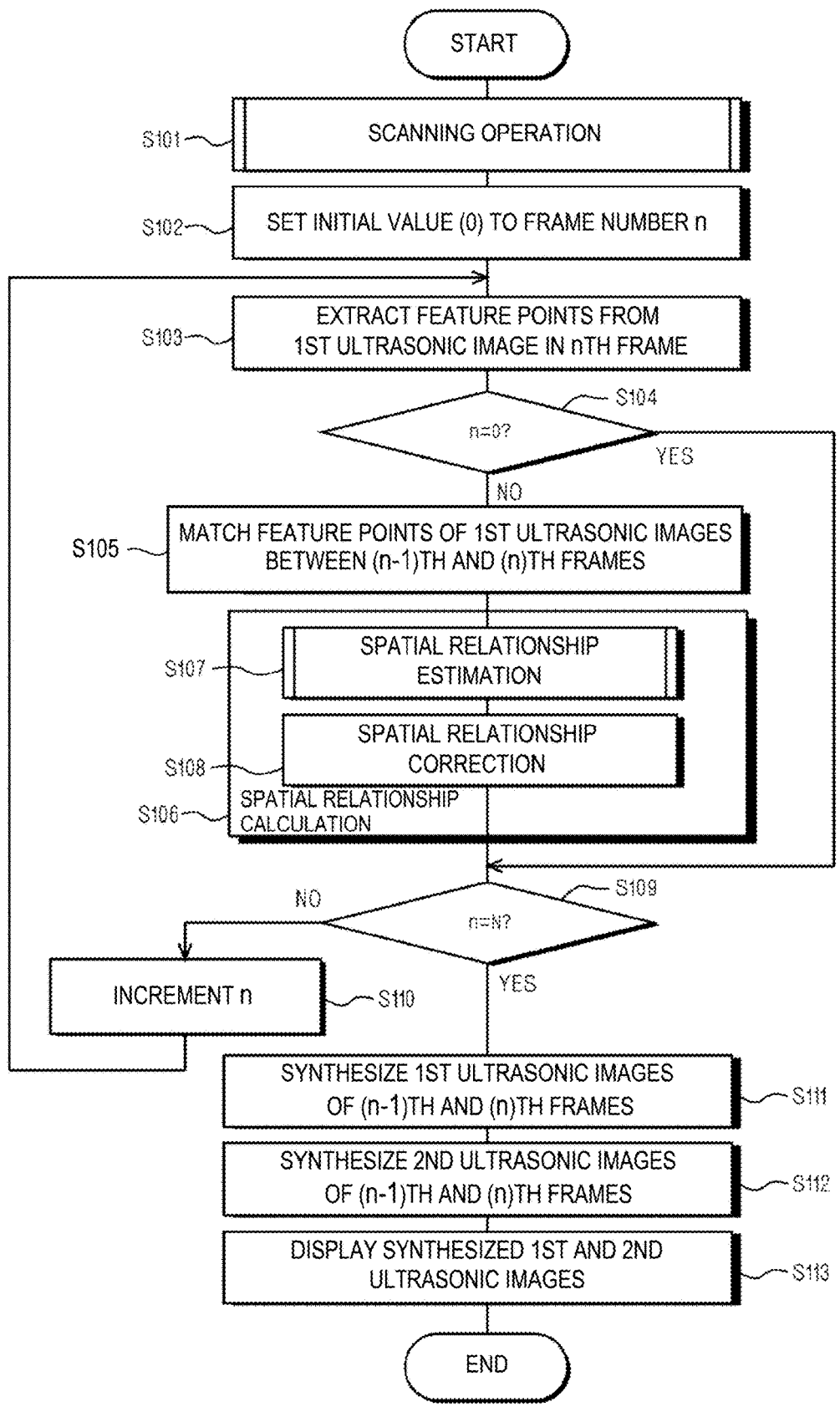
FIG. 6 is a flowchart illustrating an operating procedure of the ultrasonic imaging system according to Embodiment 1.

Next, operation of the ultrasonic imaging system according to this embodiment is described. FIG. 6 is a flowchart illustrating an operating procedure of the ultrasonic imaging system according to this embodiment. The CPU 521 of the image synthesizing device 500 may instruct a start of scan to the control device 400, and the controller 401 of the control device 400 may cause the probe 200 to perform a scanning operation according to the instruction (Step S101). During this scanning operation, the operator may move the probe 200 along the surface of the specimen, while bringing the ultrasonic transmission/reception surface 201 in contact with the surface of the specimen.

Figure 7:
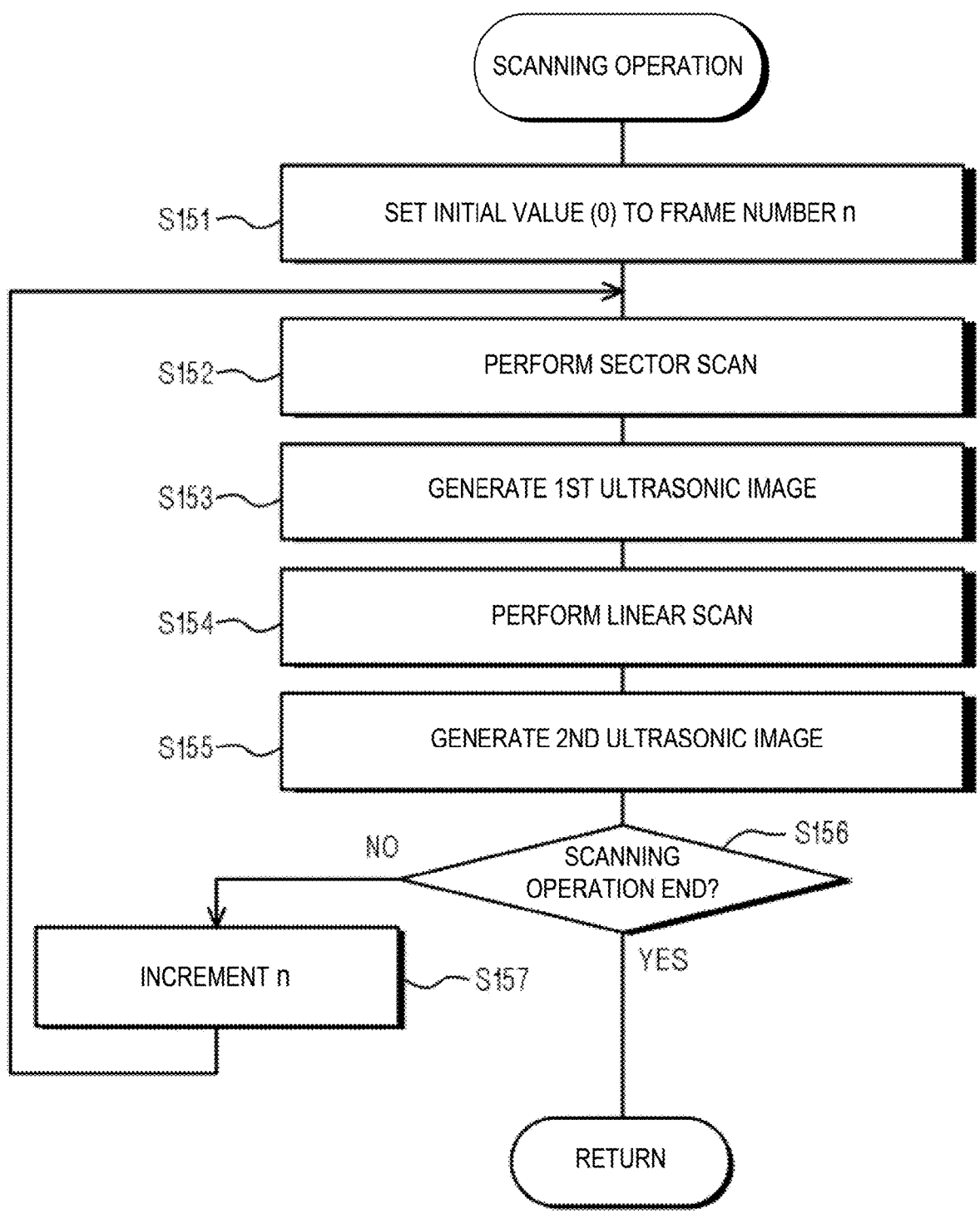
FIG. 7 is a flowchart illustrating a procedure of a scanning operation.

In the scanning operation, the controller 401 may drive the probe 200, while alternately switching between the sector scan mode and the linear scan mode. Below, the scanning operation is described in more detail. FIG. 7 is a flowchart illustrating a procedure of the scanning operation. The controller 401 may first assign an initial value (0) to a frame number n (Step S151). Next, the controller 401 may drive the probe 200 in the sector scan mode, and perform the sector scan (Step S152). In the sector scan, the probe 200 may transmit the first ultrasonic wave in the sector beam shape from the surface of the specimen in a direction perpendicular to the surface of the specimen (in a depth direction of the specimen), and receive the first ultrasonic wave reflected on the inside of the specimen.

The probe 200 may transmit the electrical signal indicative of the received first ultrasonic wave to the control device 400, and the communications interface 402 of the control device 400 may receive the received first ultrasonic wave. The image generator 404 may generate the first ultrasonic image 701 based on the electrical signal (Step S153).

After the controller 401 causes the probe 200 to perform the sector scan, it may then drive the probe 200 in the linear scan mode to perform the linear scan (Step S154). In the linear scan, the probe 200 may transmit the second ultrasonic wave in the belt-shaped (rectangular) beam shape from the surface of the specimen in the direction perpendicular to the surface of the specimen, and receive the second ultrasonic wave reflected on the inside of the specimen.

The probe 200 may transmit the electrical signal indicative of the received second ultrasonic wave to the control device 400, and the communications interface 402 of the control device 400 may receive the received second ultrasonic wave. The image generator 404 may generate the second ultrasonic image 702 based on the electrical signal (Step S155). The controller 401 may transmit the generated first and second ultrasonic images 701 and 702 to the image synthesizing device 500 from the communications interface 403 along with the frame number n. The first and second ultrasonic images 701 and 702 for one frame may be stored in each of the sector image frame memory 531 and the linear image frame memory 532 together with the frame number.

When ending the above scanning operation, the CPU 521 may instruct an end of scan to the control device 400. The controller 401 may determine whether the end-of-scan instruction is received (Step S156), and if the end-of-scan instruction is received (YES at Step S156), the scanning operation ends. On the other hand, if the end-of-scan instruction is not received, (NO at Step S156), the controller 401 may increment the frame number n (Step S157), return the processing to Step S152, and cause the probe 200 to perform the sector scan and the linear scan again.

Figure 8:
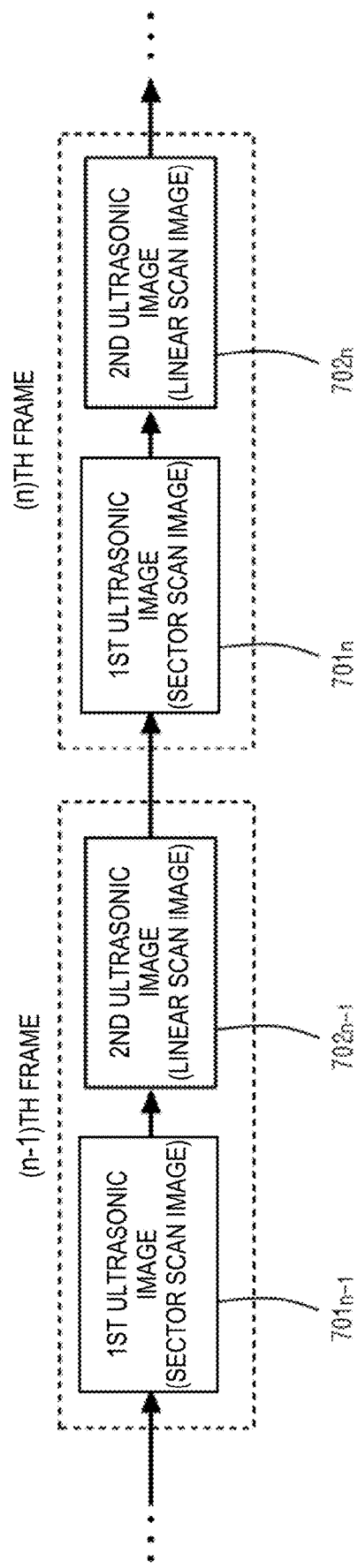
FIG. 8 is a schematic view illustrating frames of the ultrasonic imaging system according to Embodiment 1.

As described above, one cycle of the scanning operation may include one sector scan and one linear scan, and the probe 200 may perform this cycle for a plurality of times. This one cycle may correspond to one frame. FIG. 8 is a schematic view illustrating frames in the ultrasonic imaging system according to this embodiment. One frame may include one first ultrasonic image and one second ultrasonic image. Since a time interval between the sector scan and the linear scan in one cycle is significantly small, it may be considered that the sector scan and the linear scan are performed at the same position. That is, the first and second ultrasonic images included in one frame may be treated as images of the same position. Below, the first ultrasonic image in an (n-1)th frame may be expressed as $701_{n-1}$, the first ultrasonic image in an (n)th frame as $701_n$, the second ultrasonic image in the (n-1)th frame as $702_{n-1}$, and the first ultrasonic image in the (n)th frame as $702_n$.

Referring again to FIG. 6, when the above scanning operation is finished, the CPU 521 of the image synthesizing device 500 may set the initial value (0) to the frame number n (Step S102), and extract the feature points from the first ultrasonic image $701_n$ in the (n)th frame (Step S103). In this feature point extraction, a local feature amount extracting algorithm with rotational invariance, such as SIFT (Scale-Invariant Feature Transform), SURF (Speeded Up Robust Features), ORB (Oriented FAST and Rotated BRIEF), i.e., an algorithm which is capable of extracting the same local feature amount even if the image is rotated, may be used.

Next, the CPU 521 may determine whether the image to which the feature point extraction is performed is the first ultrasonic image of the first frame, i.e., whether the value of n at this time is "0" (Step S104). If the image to which the feature point extraction is performed is the first ultrasonic image of the first frame (YES at Step S104), the CPU 521 may store information on the extracted feature points in the hard disk drive 525, transit to Step S109 and shift to the feature point extraction for the next frame (frame number "1").

Figure 9:
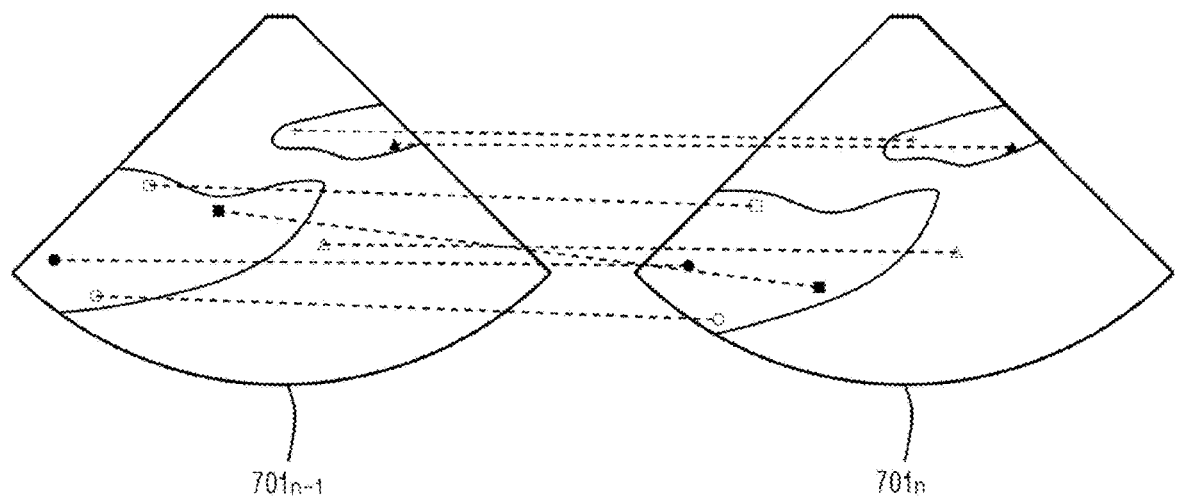
FIG. 9 is a conceptual view illustrating feature point matching.

On the other hand, if the image to which the feature point extraction is performed is not the first ultrasonic image of the first frame, i.e., if the value of n at this time is not "0" (NO at Step S104), the CPU 521 may perform matching of the feature points of the first ultrasonic image $701_{n-1}$ of the (n-1)th frame with the feature points of the first ultrasonic image $701_n$ of the (n)th frame, and determine correlations between the respective feature points (Step S105). FIG. 9 is a conceptual view illustrating processing of Step S105 (hereinafter, referred to as the "feature point matching"). In the feature point matching, between the feature points of the first ultrasonic image $701_{n-1}$ of the (n-1)th frame and the feature points of the first ultrasonic image $701_n$ of the (n)th frame, the feature points having the closest feature amounts may be associated with each other. For the calculation of the closeness of the feature amounts, the Euclid distance, the Hamming distance, etc. may be used depending on the feature point extraction technique. In FIG. 9, the same marks indicated in the first ultrasonic image $701_{n-1}$ of the (n-1)th frame and the first ultrasonic image $701_n$ of the (n)th frame may be corresponding or associated feature points. Although FIG. 9 is illustrated in a simplified manner, hundreds of feature points may be extracted in each first ultrasonic image.

Referring again to FIG. 6, the CPU 521 may then perform the spatial relationship calculation (Step S106), where the spatial relationship of the probe 200 between the (n-1)th frame and the (n)th frame is calculated. The spatial relationship calculation may include a spatial relationship estimation (Step S107) and a spatial relationship correction (Step S108).

In the spatial relationship estimation, based on the correlation between the feature points determined at Step S105, the first relational amount which is an amount of movement (positional parameter) of the first ultrasonic image between the (n-1)th frame and the (n)th frame may be calculated as an estimated value of the spatial relationship of the probe 200 between the (n-1)th frame and the (n)th frame. The first relational amount to be calculated may include translation amounts Δx and Δy which are distances in two directions x and y which are perpendicular to each other, and a rotational angle Δθ.

Below, the spatial relationship estimation is described in detail. Between the feature points $(x_k, y_k)$ on the first ultrasonic image $701_{n-1}$ of the (n-1)th frame, and the feature points $(x'_k, y'_k)$ on the first ultrasonic image $701_n$ of the (n)th frame, a relation expressed by the following Formula (1) can ideally be established. Here, k is the number of the associated feature points.

$$\begin{bmatrix} x'_k \\ y'_k \\ 1 \end{bmatrix} = \begin{bmatrix} \cos\Delta\theta & -\sin\Delta\theta & \Delta x \\ \sin\Delta\theta & \cos\Delta\theta & \Delta y \\ 0 & 0 & 1 \end{bmatrix} \begin{bmatrix} x_k \\ y_k \\ 1 \end{bmatrix} \quad (1)$$

Figure 10:
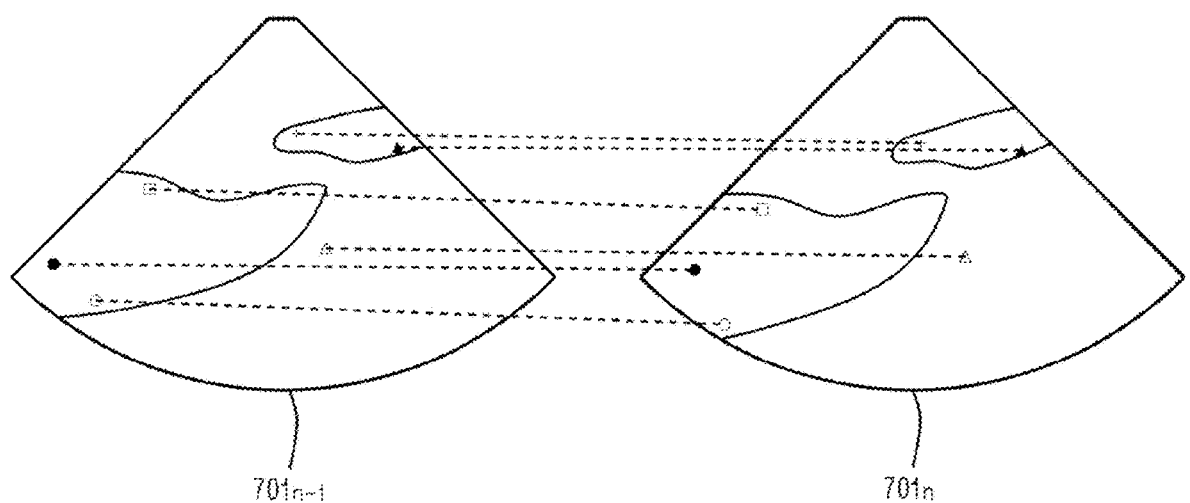
FIG. 10 is a view illustrating corresponding feature points excluding outliers.

However, the correlation between a large number of feature points cannot be satisfied with a set of spatial relationships obtained based on the corresponding feature points. This may be because an error is included in the coordinates of the feature point, and an error is included in the determined correlation itself due to the influences of noise. Therefore, the first relational amount may be to be calculated, while excluding outliers which badly influence on the calculation. The RANSAC algorithm can be used for the exclusion of the outliers, and a nonlinear least-squares method, such as the Gauss Newton method or Levenberg-Marquardt method, can be used for the calculation of the spatial relationship. FIG. 10 is a view illustrating the corresponding feature points excluding the outliers. By excluding the outliers, the first relational amount can be calculated accurately using the accurately associated feature points.

Figure 11:
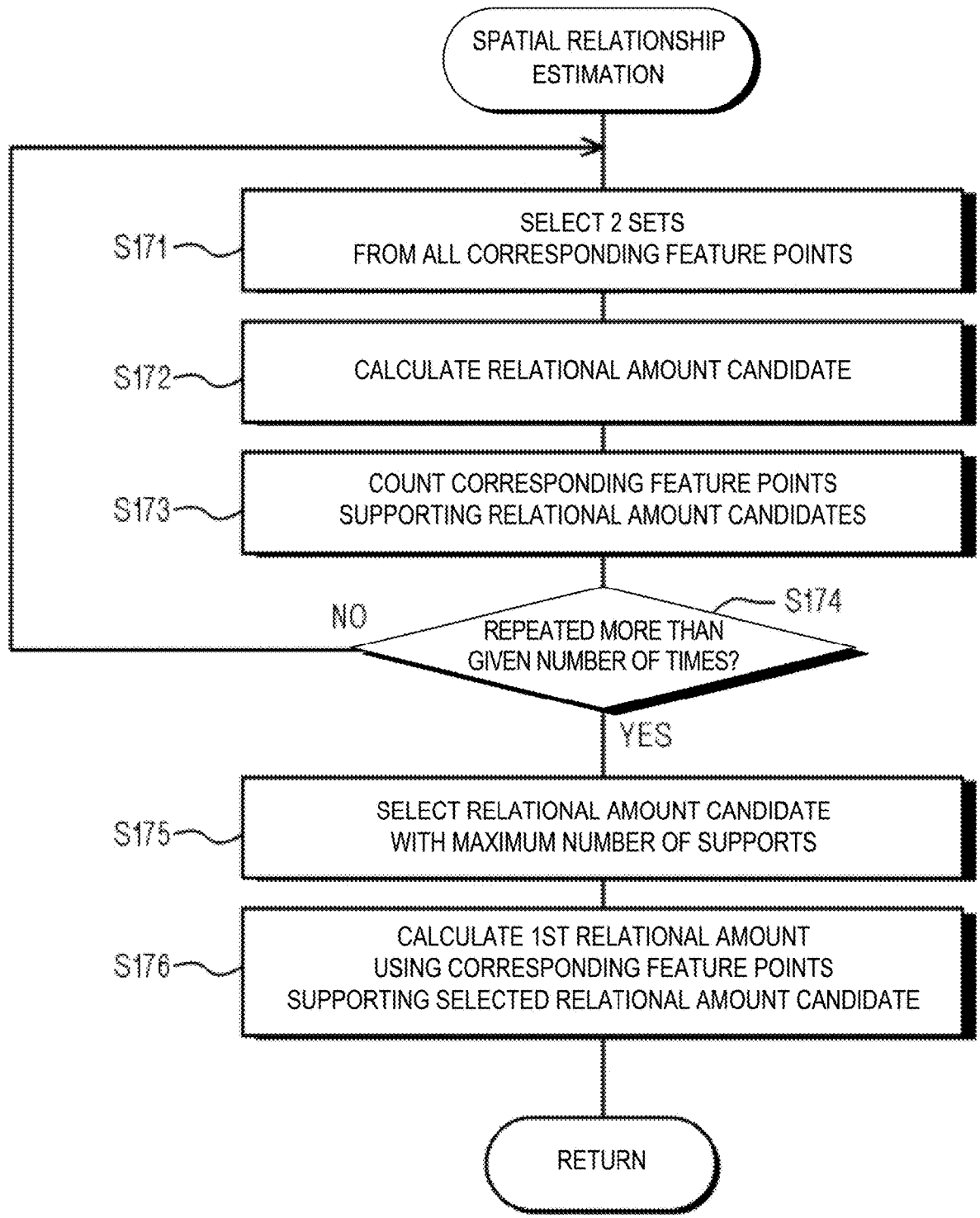
FIG. 11 is a flowchart illustrating a procedure of a spatial relationship calculation.

FIG. 11 is a flowchart illustrating a procedure of the spatial relationship estimation. In the spatial relationship estimation, the CPU 521 may first select two sets at random from all the corresponding feature points (Step S171), and calculate, based on the obtained two sets of feature points, a relational amount candidate which is a candidate value of the spatial relationship (the amount of movement) of the probe 200 between the (n-1)th frame and the (n)th frame (Step S172).

Next, the CPU 521 may calculate a square error of all the corresponding feature points (hereinafter, referred to as the "corresponding feature points") using the calculated relational amount candidates, and count the number of the corresponding feature points of which the error becomes below a given threshold because the corresponding feature points support the relational amount candidates (Step S173). The following Formula (2) may be used for the calculation of the square error $e_k$.

$$e_k = (x'_k - x_k)^2 + (y'_k - y_k)^2 \quad (2)$$

The CPU 521 may determine whether the number of repetition reaches a given number (Step S174), and if the number of repetition does not reach the given number (NO at Step S174), it may return the processing to Step S171. Therefore, the processings at Steps S171-S173 may be repeatedly performed to obtain a plurality of relational amount candidates.

If the number of repetition reaches the given number (YES at Step S174), the CPU 521 may select the relational amount candidate with the maximum number of supports, among all the relational amount candidates (Step S175).

Next, the CPU 521 may calculate the final first relational amount using the corresponding feature points which support the relational amount candidate selected at Step S175 (Step S176), and end the spatial relationship estimation.

At Steps S172 and S176, the first relational amount (or the relational amount candidate) may be calculated using a plurality of sets (the number of sets is K) of corresponding feature points. An error function defined by the following Formula (3) may be used for the calculation of such a first relational amount (or the relational amount candidate).

$$E = \frac{1}{2}\sum_{k=1}^{K} e_k = \frac{1}{2}\sum_{k=1}^{K}\{(x'_k - x_k)^2 + (y'_k - y_k)^2\} \quad (3)$$

The first relational amount (or the relational amount candidate) which minimizes the error function expressed by Formula (3) may be calculated by the nonlinear least-squares method, such as the Gauss Newton method or Levenberg-Marquardt method. Since two equations are obtained from Formula (1), the first relational amount (or the relational amount candidate) can be calculated, if there are two or more sets of corresponding feature points. The number of sets of corresponding feature points may be K=2 at Step S172, and K≥2 at Step S176.

There may be the following advantages in the calculation of the first relational amount based on the feature points using the first ultrasonic image which is the sector scan image. (1) When the probe 200 with a smaller probe width is used, the imaging range in the linear scan may become smaller, and the calculation of the accurate rotational angle Δθ may become difficult in the calculation of the spatial relationship using the linear scan image (the second ultrasonic image). In this regard, Δθ can be calculated with sufficient accuracy by using the sector scan image with a larger imaging range. (2) In the matching of local feature points, since the matching is performed not based on coordinates but based on the degree of similarity of the feature amounts, the spatial relationship of both the frames can be calculated without taking the imaging positions of the (n-1) and (n)th frames into consideration.

By the above spatial relationship estimation, the first relational amount which is the estimated value of the spatial relationship of the probe 200 between the (n-1)th frame and the (n)th frame can be calculated. If the first relational amount is large, i.e., if the distance between the position of the probe 200 in the (n-1)th frame and the position of the probe 200 in the (n)th frame is large, even if a sufficient overlapping area in the first ultrasonic image which is the sector scan image can be secured, a sufficient overlapping area in the second ultrasonic image which is the linear scan image cannot be secured, and a subsequent correlation value calculation and an image synthesis of the second ultrasonic image may not be performed accurately. Therefore, in such a case, the processing of image correlation can be skipped by considering the processing as an error, or by lowering the synthetic accuracy, and the image synthesis can be carried out using the first relational amount obtained by the spatial relationship estimation as it is.

Referring again to FIG. 6, after the spatial relationship estimation, the CPU 521 may perform the spatial relationship correction (Step S108). In the spatial relationship correction, the second relational amount, which is obtained by correcting the first relational amount calculated by the spatial relationship estimation based on the image correlation between the second ultrasonic images $702_{n-1}$ and $702_n$ of the (n-1)th frame and the (n)th frame, may be calculated. In this embodiment, the translation amounts Δx and Δy may be corrected among the first relational amounts in the spatial relationship correction.

Below, the spatial relationship correction is described in detail. The CPU 521 may apply the translation and the rotation to the second ultrasonic image $702_n$ of the (n)th frame using the first relational amount (the translation amounts Δx and Δy, and the rotational angle Δθ) calculated by the spatial relationship estimation. Below, the second ultrasonic image after this movement may be referred to as (n')th frame image.

Figure 12:
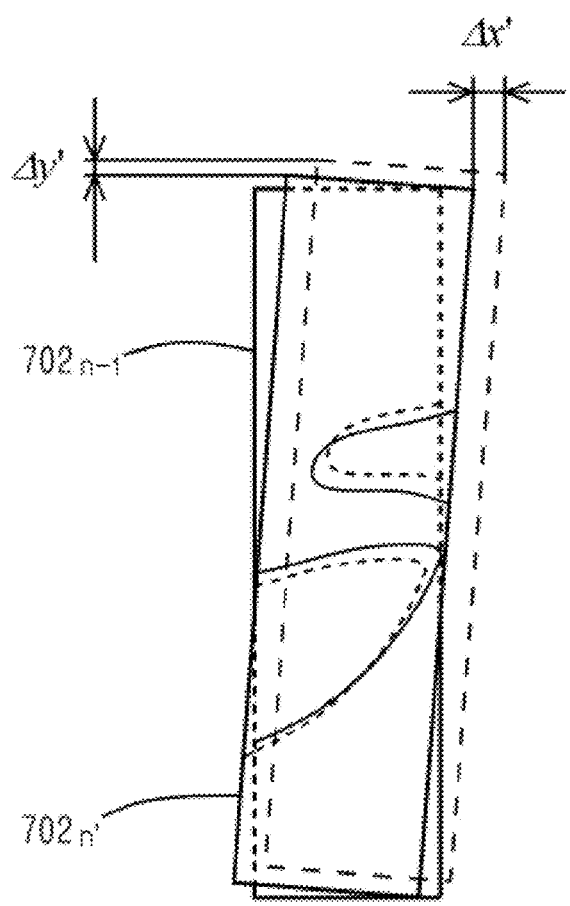
FIG. 12 is a conceptual view illustrating a spatial relationship correction.

FIG. 12 is a conceptual view illustrating the spatial relationship correction. Next, the CPU 521 may move the (n')th frame image $702_{n'}$ by Δx' or Δy' in the x-axis or y-axis direction, compare the image after the movement with the second ultrasonic image $702_{n-1}$ of the (n-1)th frame, and calculate an image correlation value based on a luminance value. For the calculation of the correlation value, SAD (Sum of Absolute Difference), ZNCC (Zero-mean Normalized Cross-Correlation), etc. can be used. The CPU 521 may repeatedly perform the movement of the (n')th frame image and the calculation of the image correlation value, search for a given search range (e.g., ±20 pixels) for both the x-axis and the y-axis, and acquire the image correlation value at each position. When the image correlation value at each position is calculated, the CPU 521 may determine the position where the image correlation value becomes the maximum as final translation amounts $\Delta x$ and $\Delta y$.

Since the linear scan image is higher in the resolution than the sector scan image and there is less speckle, the amount of translation can be corrected with sufficient accuracy by using the linear scan image. The second relational amount ($\Delta x$, $\Delta y$, $\Delta \theta$) calculated by the above spatial relationship correction may be stored in the hard disk drive 525 along with the frame number n.

Referring again to FIG. 6, next, the CPU 521 may determine whether the value of n matches with the final frame number N (Step S109). If n does not match with the maximum value N (NO at Step S109), the CPU 521 may increment n (Step S110), and return the processing to Step S103.

If n matches with the maximum value N (YES at Step S109), the CPU 521 may synthesize the first ultrasonic images $701_{n-1}$ and $701_n$ of the (n-1)th frame and the (n)th frame by using the second relational amount (Step S111), and similarly synthesize the second ultrasonic images $702_{n-1}$ and $702_n$ of the (n-1)th frame and the (n)th frame by using the second relational amount (Step S112). The CPU 521 may display on the display unit the synthesized first ultrasonic image and the synthesized second ultrasonic image (Step S113), and end the processing.

By configuring as described above, since the first ultrasonic image of the large imaging range is acquired by the sector scan which is a wide-angle imaging, and the first relational amount is calculated using the first ultrasonic image, the first relational amount can be calculated securely, even when the ultrasonic imaging of the part of a human body with a large curvature, such as a leg or an upper limb, is carried out by using the probe with the small width. Moreover, since the second relational amount which is obtained by correcting the first relational amount is calculated using the second ultrasonic image obtained by the high resolution linear scan, the accurate second relational amount can be obtained.

Embodiment 2

In this embodiment, an angle sensor may be provided to the probe, a direction of the probe is acquired by the angle sensor, and a rotational angle of the probe between two sector scans is calculated. The sector scan and the linear scan may alternately be repeated by the probe. The first relational amount which is the distance between two positions (the amount of translation) may be calculated based on the two sector scan images obtained by the two sector scans at the two positions. The second relational amount (the amount of translation) which is obtained by correcting the first relational amount based on the two linear scan images obtained by the twice linear scans at the two positions may be calculated. The sector scan image or the linear scan image may be synthesized based on the second relational amount and the rotational angle obtained based on the angle sensor.

<Configuration of Ultrasonic Imaging System>

Figure 13:
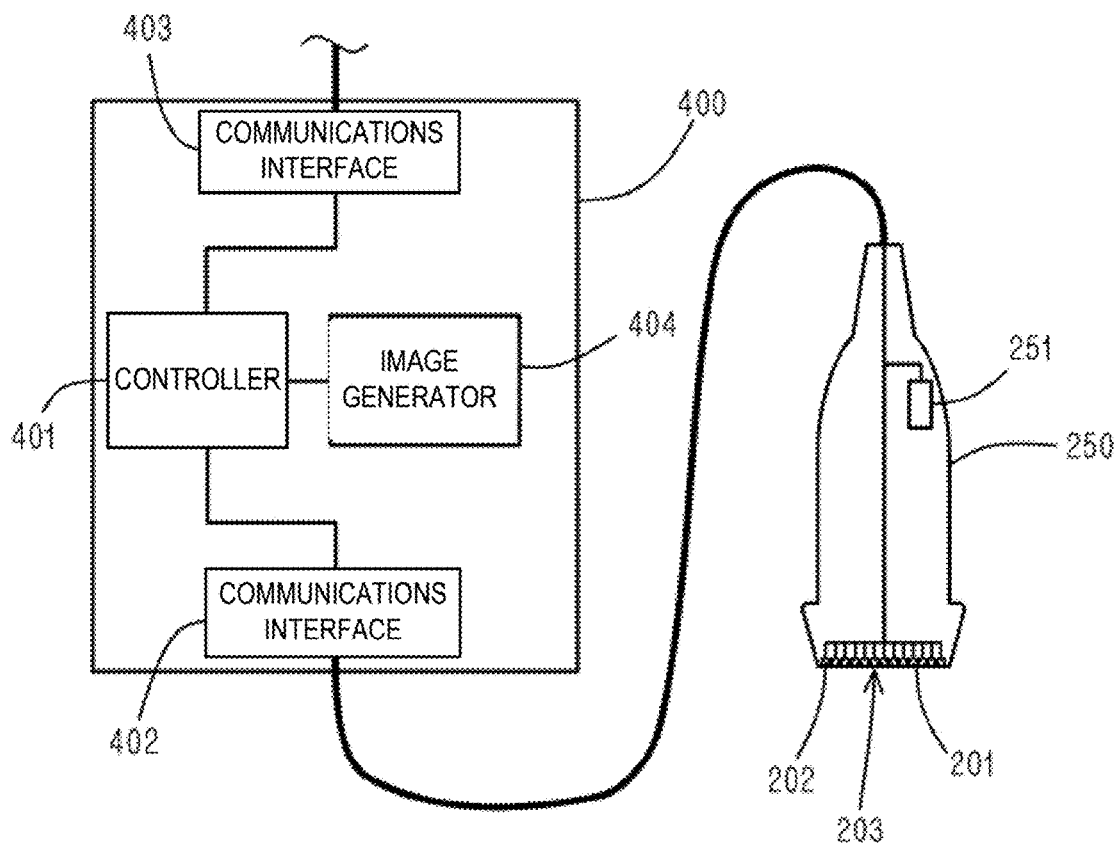
FIG. 13 is a schematic view illustrating a configuration of a probe and a control device of an ultrasonic imaging system according to Embodiment 2.

FIG. 13 is a schematic view illustrating a configuration of a probe 250 and the control device 400. The probe 250 may include an angle sensor 251. The angle sensor 251 may detect an inclination from the vertical direction of the probe 250, i.e., a direction in which the ultrasonic transmission/reception surface 201 faces. Since other configurations of the ultrasonic imaging system according to this embodiment are similar to the configuration of the ultrasonic imaging system 100 according to Embodiment 1, the same reference characters may be assigned to the same components to omit the description thereof.

<Operation of Ultrasonic Imaging System>

Figure 14:
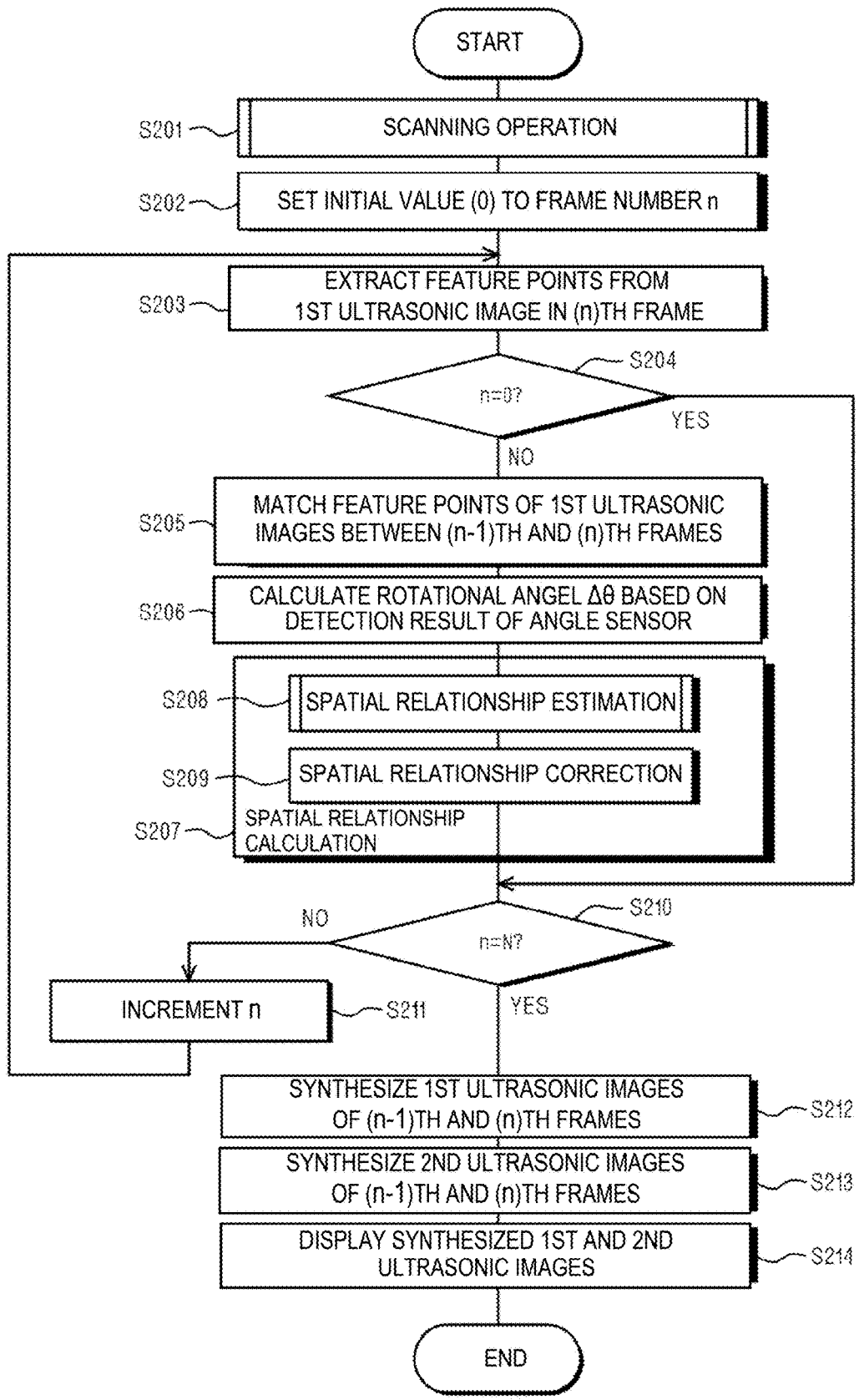
FIG. 14 is a flowchart illustrating an operating procedure of the ultrasonic imaging system according to Embodiment 2.

Next, operation of the ultrasonic imaging system according to this embodiment is described. FIG. 14 is a flowchart illustrating an operating procedure of the ultrasonic imaging system according to this embodiment. The CPU 521 of the image synthesizing device 500 may instruct a start of scan to the control device 400, and the controller 401 of the control device 400 may cause the probe 250 to perform a scanning operation according to this instruction (Step S201). During this scanning operation, the operator may move the probe 250 along the surface of the specimen, while bringing the ultrasonic transmission/reception surface 201 in contact with the surface of the specimen.

Figure 15:
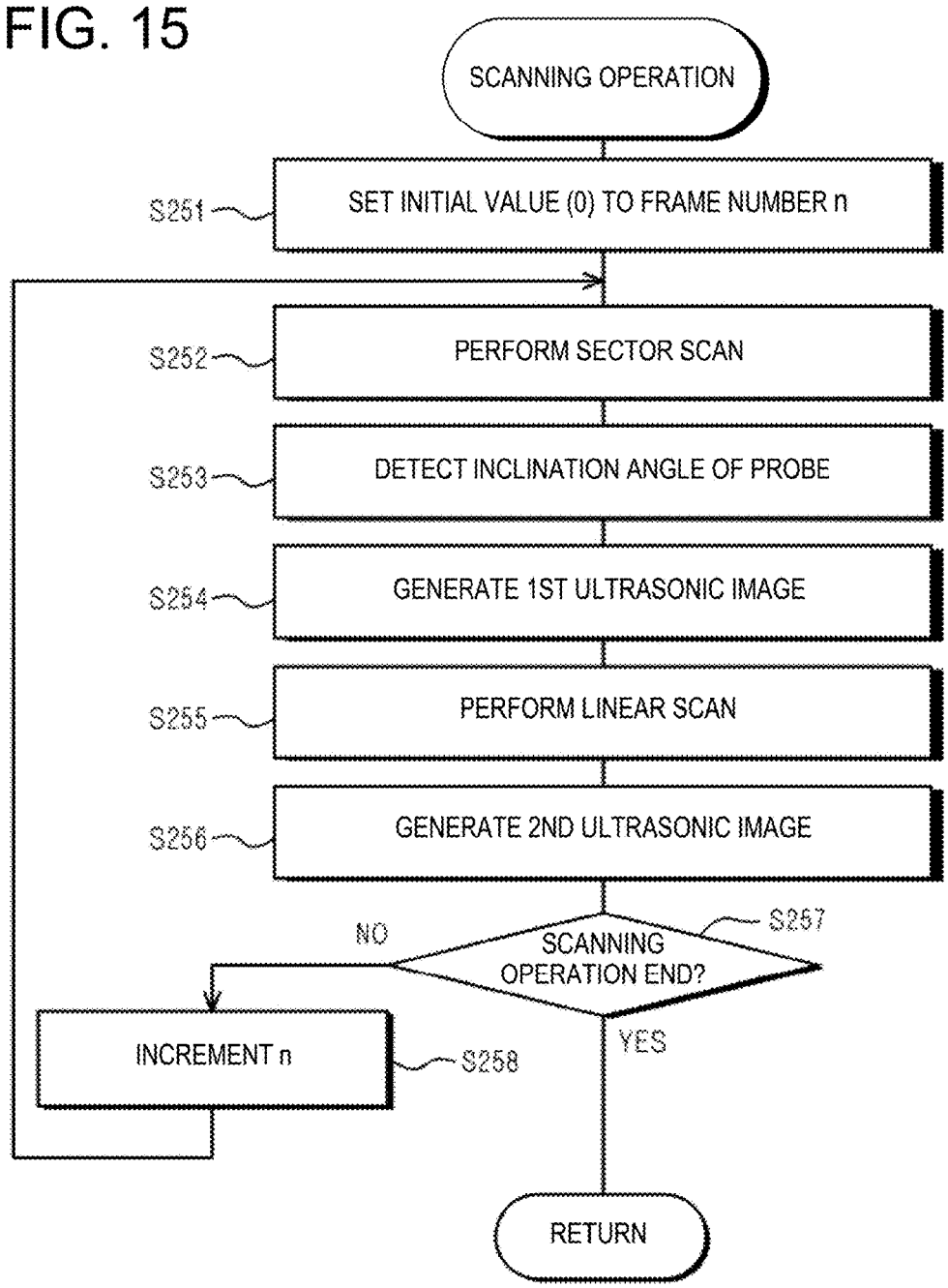
FIG. 15 is a flowchart illustrating a procedure of a scanning operation.

In the scanning operation, the controller 401 may drive the probe 250, while alternating the mode between the sector scan mode and the linear scan mode. Below, the scanning operation is described in more detail. FIG. 15 is a flowchart illustrating a procedure of the scanning operation. The controller 401 may first assign the initial value (0) to the frame number n (Step S251). Next, the controller 401 may drive the probe 250 in the sector scan mode to perform the sector scan (Step S252). In the sector scan, the probe 250 may transmit the first ultrasonic wave by scanning a sector-shaped beam from the surface of the specimen in the vertical direction of the surface of the specimen, and receive the first ultrasonic wave reflected on the inside of the specimen. Moreover, the angle sensor 251 may detect an inclination angle from the vertical direction of the probe 250 during the sector scan (Step S253).

The probe 250 may transmit an electrical signal indicative of the received first ultrasonic wave and an electrical signal indicative of the inclination angle to the control device 400, and the communications interface 402 of the control device 400 may receive these electrical signals. The image generator 404 may generate the first ultrasonic image 701 based on the electrical signals (Step S254).

After the controller 401 causes the probe 250 to perform the sector scan, it may then drive the probe 250 in the linear scan mode to perform the linear scan (Step S255). In the linear scan, the probe 250 may transmit the second ultrasonic wave of the belt-like (rectangular) beam shape from the surface of the specimen in the vertical direction of the surface of the specimen, and receive the second ultrasonic wave reflected on the inside of the specimen.

The probe 250 may transmit an electrical signal indicative of the received second ultrasonic wave to the control device 400, and the communications interface 402 of the control device 400 may receive the electrical signal. The image generator 404 may generate the second ultrasonic image 702 based on the electrical signal (Step S256). The controller 401 may transmit the generated first and second ultrasonic images 701 and 702 to the image synthesizing device 500 from the communications interface 403 along with the frame number n and the inclination angle. The first and second ultrasonic images 701 and 702 for one frame may be stored in each of the sector image frame memory 531 and the linear image frame memory 532 together with the frame number. Moreover, the inclination angle may be stored in the hard disk drive 525 together with the frame number.

When ending the above scanning operation, the CPU 521 may instruct an end of scan to the control device 400. The controller 401 may determine whether the end-of-scan instruction is received (Step S257), and if the end-of-scan instruction is received (YES at Step S257), it may then end the scanning operation. On the other hand, if the end-of-scan instruction is not received (NO at Step S257), the controller 401 may increment the frame number n (Step S258), and return the processing to Step S252 to cause the probe 250 to again perform the sector scan and the linear scan.

As described above, one cycle of the scanning operation may include one sector scan and one linear scan, and the probe 250 may perform this cycle for a plurality of times. One cycle may correspond to one frame. One frame may include one first ultrasonic image 701 and one second ultrasonic image 702. Since a time interval between the sector scan and the linear scan in one cycle is significantly small, the sector scan and the linear scan may be considered to be performed at the same position. That is, the first and second ultrasonic images 701 and 702 included in one frame may be treated as images at the same position.

Referring again to FIG. 14, since processings at Steps S202 to S205 are similar to the processings at Steps S102 to S105 described in Embodiment 1, the description thereof is omitted.

The CPU 521 may calculate the rotational angle $\Delta\theta$ based on the inclination angle detected by the angle sensor 251 (Step S206). The rotational angle $\Delta\theta$ may be calculated as a difference between the inclination angle between the (n-1)th frame and the (n)th frame. Note that, instead of the angle sensor 251, a direction sensor which detects an azimuth using geomagnetism may be provided to the probe 250, and the rotational angle $\Delta\theta$ may be calculated based on the azimuths detected by the direction sensor in the (n-1)th frame and the (n)th frame.

Next, the CPU 521 may perform the spatial relationship calculation (Step S207). The spatial relationship calculation may include the spatial relationship estimation (Step S208) and the spatial relationship correction (Step S209). In this embodiment, the positional parameters $\Delta x$ and $\Delta y$ excluding the rotational angle may be calculated based on the first ultrasonic image as the first relational amount in the spatial relationship estimation. The method of calculating the translation amounts $\Delta x$ and $\Delta y$ may be similar to that described in Embodiment 1.

Since processings at Steps S209 to S214 are similar to the processings at Steps S108 to S113 described in Embodiment 1, the description thereof is omitted.

By configuring as described above, the rotational angle of the probe 250 can be obtained with sufficient accuracy using the inclination angle detected by the angle sensor 251, and thereby, the accurate image synthesis can be performed. Moreover, since it is not necessary to calculate the rotational angle by the image processing, the computational complexity may be reduced.

Other Embodiments

In Embodiments 1 and 2 described above, although the first relational amount is corrected using the second ultrasonic image, the present disclosure is not limited to this configuration. The first relational amount calculated from the first ultrasonic image can be used for the image synthesis, without being corrected. Moreover, although the translation amounts $\Delta x$ and $\Delta y$ are used as the targets to be corrected among the first relational amounts, the present disclosure is not limited to this configuration. The rotational angle $\Delta\theta$ may also be the candidate for correction.

Moreover, in Embodiments 1 and 2 described above, the sector scan may first be performed and the linear scan may then be performed in each frame, the first relational amount may be calculated using the first ultrasonic images which are first obtained in the (n-1)th frame and the (n)th frame, and the second relational amount which is obtained by correcting the first relational amount may be calculated using the second ultrasonic images which are obtained thereafter in the (n-1)th frame and the (n)th frame. However, the present disclosure is not limited to this configuration. In each frame, the linear scan may be first performed and the sector scan may then be performed. The first relational amount may be calculated using the first ultrasonic images obtained later on in the (n-1)th frame and the (n)th frame, and the second relational amount which is obtained by correcting the first relational amount may be calculated using the second ultrasonic images previously obtained in the (n-1)th frame and the (n)th frame.

Moreover, other scans may also be performed in one cycle, in addition to the sector scan and the linear scan. In this case, in addition to the first and second ultrasonic images, other ultrasonic images may be also included in one frame. Note that, in order to perform the image synthesis, it may be necessary for an image to include an overlapping area ranging over cycles. However, if it is configured in this way, since a time required for one cycle becomes longer, there may be a possibility that the overlapping area may not be fully secured. For this reason, it may be desirable to restrict a moving speed of the probe in consideration of the time required for one cycle. For example, an error may be notified if the speed becomes such that probe moves more than a half of the probe width during the time required for one cycle.

Moreover, in Embodiments 1 and 2, although the images of the two continuous frames are synthesized, the present disclosure is not limited to this configuration. As long as there are two different frames, they may not be continuous. For example, the ultrasonic images of the (n-2)th frame and the (n)th frame may be synthesized. In this case, based on the first and second ultrasonic images of the (n-2)th frame and the (n)th frame, a spatial relationship (the second relational amount) of the probe in the (n-2)th frame and the (n)th frame may be calculated, and based on the calculated spatial relationship, at least one of the first and the second ultrasonic images of the (n-2)th frame and the (n)th frame may be synthesized. Note that it may be also necessary in this case to secure the overlapping area of the image ranging over two different frames. Therefore, the moving speed may be restricted to become so that it moves less than a half of the probe width during a time corresponding to the two frames.

Moreover, in Embodiments 1 and 2, although both the first and second ultrasonic images are synthesized, the present disclosure is not limited to this configuration. One of the first and second ultrasonic images may be synthesized. For example, the operator may select the target to be synthesized from the first and second ultrasonic images, and the selected images are synthesized.

Figure 16:
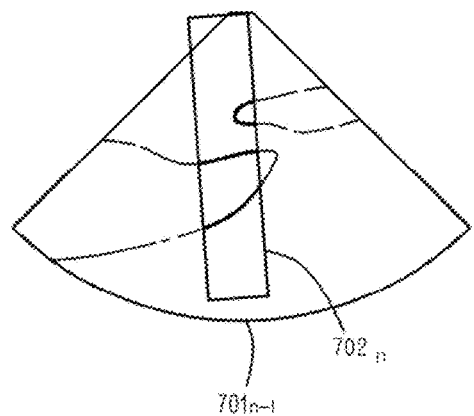
FIG. 16 is a view illustrating one example of synthesis of a first ultrasonic image and a second ultrasonic image.

Moreover, in Embodiments 1 and 2, although the first ultrasonic images are synthesized or the second ultrasonic images are synthesized, the first ultrasonic image and the second ultrasonic image may also be synthesized. For example, as illustrated in FIG. 16, by synthesizing the first ultrasonic image $701_{n-1}$ of the (n-1)th frame and the second ultrasonic image $702_n$ of the (n)th frame, quality of the image can be improved in the imaging range of the second ultrasonic image, while maintaining the imaging range of the first ultrasonic image.

Moreover, in Embodiments 1 and 2, although the sector scan of the fan-shaped imaging range and the linear scan of the belt-shaped imaging range are performed, the present disclosure is not limited to this configuration. The scan may be other than the sector scan image and the linear scan image, as long as one of the images is larger in the imaging range and lower in the resolution, and the other image is smaller in the imaging range and higher in the resolution. As long as the scan mode is changeable in the imaging angle range, the two kinds of scans may be performed by switching the imaging angle range, while fixing the mode to this scan mode. For example, the scan mode is fixed to the sector scan mode, and the drive frequency is fixed, and the angle range (imaging range) is switched. By configuring in this way, the sector scan image (the first ultrasonic image) with the larger imaging range and the lower resolution can be obtained by the scan with the larger angle range, and the sector scan image (the second ultrasonic image) with, the smaller imaging range and higher resolution can be obtained by the scan with the smaller angle range. That is, the scan mode and the drive frequency may be fixed, and each of the scan of the first ultrasonic wave and the scan of the second ultrasonic wave may be performed by switching the imaging range. Alternatively, while the scan mode being fixed, the scan of the first ultrasonic wave may be performed drive with larger imaging range and the lower drive frequency high, and the scan of the second ultrasonic wave may be performed with the smaller imaging range and the high drive frequency. Even in such a case, the first ultrasonic image with the larger imaging range and the lower resolution, and the second ultrasonic image with the larger imaging range and the higher resolution can be obtained. Further, while the drive frequency being fixed, two kinds of scans may also be performed by switching the scan mode. For example, while the drive frequency being fixed, by performing each of the sector scan and the linear scan, the sector scan image (the first ultrasonic image) with the larger imaging range and the lower resolution, the linear scan image (the second ultrasonic image) with smaller imaging range and the higher resolution can be obtained. Alternatively, two kinds of ultrasonic scans may be performed using a convex-type probe.

Moreover, in Embodiments 1 and 2, although the first relational amount is calculated by the feature point matching, and the second relational amount which is obtained by correcting the first relational amount by the image correlation is calculated, the present disclosure is not limited to this configuration. The first relational amount may be calculated by a pattern matching other than the feature point matching, for example, by the image correlation, and the second relational amount may be calculated by a pattern matching other than the image correlation, for example, by the feature point matching.

Moreover, in Embodiments 1 and 2, although the ultrasonic imaging device 300 is comprised of the control device 400 and the image synthesizing device 500, the present disclosure is not limited to this configuration. A sole ultrasonic imaging device may also be constituted by being provided with both the functions of the control device 400 and the image synthesizing device 500. Moreover, although the calculation of the spatial relationship and the image synthesis are implemented by the software, the present disclosure is not limited to this configuration. These processings may also be performed by an image processor.

Figure 17:
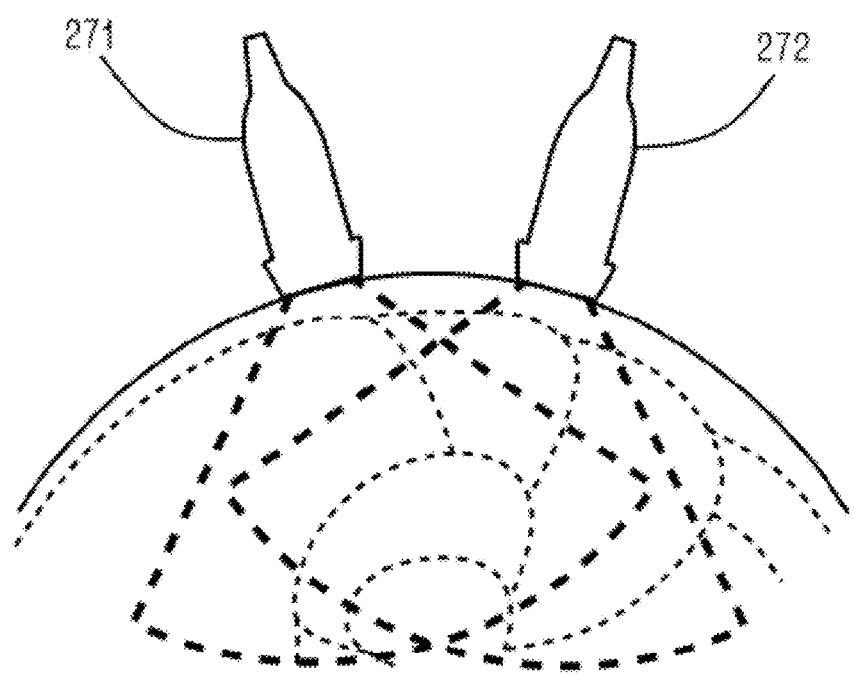
FIG. 17 is a view illustrating one example of scans by a plurality of probes.

Moreover, in Embodiments 1 and 2, although the measurement is performed, while the probe is moved, the number of probes may not be one, as long as two frames can be imaged at different positions. For example, a plurality of probes may be used as illustrated in FIG. 17. In this case, the sector scan and the linear scan may be performed by a probe 271, and the sector scan and the linear scan may be performed by a probe 272. Based on two sector scan images (the first ultrasonic images) and two linear scan images (the second ultrasonic images) which are respectively obtained by the probes 271 and 272, a relationship between the imaging positions of the probes 271 and 272 may be calculated, and based on this spatial relationship, the first or second ultrasonic image obtained by the probe 271 and the first or second ultrasonic image obtained by the probe 272 may be synthesized.

INDUSTRIAL APPLICABILITY

The ultrasonic imaging system, the ultrasonic imaging device, the ultrasonic imaging method, and the image synthesizing program of the present disclosure may be useful as ultrasonic imaging systems, ultrasonic imaging devices, and ultrasonic imaging methods, which transmit the ultrasonic wave into the specimen, such as the human body, receive the reflected ultrasonic wave to image the inside of the specimen, and image synthesizing programs which causes the computer to synthesize the ultrasonic images.

The invention claimed is:

1. An ultrasonic imaging system, comprising:
   a probe configured to continuously and alternatingly transmit fan-shaped first and belt-shaped second ultrasonic waves into a specimen through the surface of the specimen while moving along an outer surface of a cross section of the specimen and continuously and alternatingly receive the fan-shaped first and belt-shaped second ultrasonic waves reflected on the inside of the specimen; and
   processing circuitry configured to:
      in each of first and second frames taken at respective probe positions on the outer surface of the cross section, generate a first ultrasonic image, which is a sector scan image, based on the fan-shaped first ultrasonic wave received by the probe to thereby generate two first ultrasonic images;
      in each of the first and second frames, generate a second ultrasonic image, which is a linear scan image, based on the belt-shaped second ultrasonic wave received by the probe to thereby generate two second ultrasonic images;
      calculate a first relational amount that is an estimated value of the relationship between two different probe positions on the surface of the specimen, based on the two first ultrasonic images at the two probe positions;
      calculate a second relational amount resulting from correcting the first relational amount based on the two second ultrasonic images at the two probe positions; and
      synthesize one of the first and second ultrasonic images at one of the two probe positions with the one of the first and second ultrasonic images at the other one of the two probe positions based on the second relational amount.

2. The ultrasonic imaging system of claim 1, wherein the probe transmits the fan-shaped first and belt-shaped second ultrasonic waves by different scanning modes.

3. The ultrasonic imaging system of claim 1, wherein the probe transmits the fan-shaped first and belt-shaped second ultrasonic waves at different frequencies.

4. An ultrasonic imaging device, comprising:
processing circuitry configured, using a probe configured to continuously and alternatingly transmit fan-shaped first and belt-shaped second ultrasonic waves into a specimen through the surface of the specimen while moving along an outer surface of a cross section of the specimen and continuously and alternatingly receive the fan-shaped first and belt-shaped second ultrasonic waves reflected on the inside of the specimen, to:
in each of first and second frames taken at respective probe positions on the outer surface of the cross section, generate a first ultrasonic image, which is a sector scan image, based on the fan-shaped first ultrasonic wave received by the probe;
in each of the first and second frames, generate a second ultrasonic image, which is a linear scan image, based on the belt-shaped second ultrasonic wave received by the probe;
calculate a first relational amount that is an estimated value of the relationship between two different probe positions on the surface of the specimen, based on the two first ultrasonic images at the two probe positions;
calculate a second relational amount resulting from correcting the first relational amount based on the two second ultrasonic images at the two probe positions; and
synthesize one of the first and second ultrasonic images at one of the two probe positions with the one of the first and second ultrasonic images at the other one of the two probe positions based on the second relational amount.

5. The ultrasonic imaging device of claim 4, wherein the processing circuitry calculates the first relational amount at least in part by calculating a distance between the two positions in two directions intersecting each other.

6. The ultrasonic imaging device of claim 5, wherein the processing circuitry calculates the first relational amount at least in part by calculating a rotational angle of the probe in a plane extending in the two directions.

7. The ultrasonic imaging device of claim 5,
wherein the processing circuitry is further configured to calculate the rotational angle of the probe at each of the two positions in the plane extending in the two directions, based on an angle detected at each of the two positions by a sensor configured to detect a direction of the probe in which the probe faces, and
wherein the processing circuitry synthesizes one of the first and second ultrasonic images at one of the two positions with the one of the first and second ultrasonic images at the other position, based on the distance calculated by the processing circuitry and the rotational angle calculated by the processing circuitry.

8. The ultrasonic imaging device of claim 4, wherein the processing circuitry calculates the first relational amount by extracting a feature point of each of the two first ultrasonic images and determining a correlation of the feature points between the two first ultrasonic images.

9. The ultrasonic imaging device of claim 4, wherein the processing circuitry calculates the second relational amount based on a correlation of a luminance distribution of the two second ultrasonic images.

10. The ultrasonic imaging device of claim 4,
wherein the processing circuitry synthesizes one of the first and second ultrasonic images at one of the two positions with the one of the first and second ultrasonic images at the other position, based on the second relational amount calculated by the processing circuitry.

11. The ultrasonic imaging device of claim 5,
wherein the processing circuitry synthesizes one of the first and second ultrasonic images at one of the two positions with the one of the first and second ultrasonic images at the other position, based on the second relational amount calculated by the processing circuitry.

12. An ultrasonic imaging method, comprising the steps of:
causing a probe configured to continuously and alternatingly transmit and receive ultrasonic waves, to transmit fan-shaped first and belt-shaped second ultrasonic waves into a specimen at two different positions of the surface of the specimen while moving along an outer surface of a cross section of the specimen and continuously and alternatingly receive the fan-shaped first and belt-shaped second ultrasonic waves reflected on the inside of the specimen at each of the two positions;
generating two first ultrasonic images, which are sector scan images, based on the fan-shaped first ultrasonic waves received by the probe at the two positions on the outer surface of the cross section;
generating two second ultrasonic images, which are linear scan images, based on the belt-shaped second ultrasonic waves received by the probe at the two positions on the cross section;
calculating a first relational amount that is an estimated value of the relationship between two different probe positions on the surface of the specimen, based on the two first ultrasonic images at the two probe positions;
calculating a second relational amount resulting from correcting the first relational amount based on the two second ultrasonic images at the two probe positions; and
synthesizing one of the first and second ultrasonic images at one of the two positions with the one of the first and second ultrasonic images at the other position based on the second relational amount.

13. An image synthesizing program causing a computer to execute processing of synthesizing a plurality of ultrasonic images obtained by imaging inside of a specimen, the program causing the computer to execute the steps of:
calculating, on the basis of two first ultrasonic images, which are sector scan images, generated based on fan-shaped first ultrasonic waves received by a probe at two different positions of the surface of the specimen while moving along an outer surface of a cross section of the specimen and two second ultrasonic images, which are linear scan images, generated based on belt-shaped second ultrasonic waves received by the probe at the two positions on the outer surface of the cross section, a first relational amount and a second relational amount, the probe continuously and alternatingly transmitting the fan-shaped first and belt-shaped second ultrasonic waves into the specimen through the surface of the specimen and continuously and alternatingly receiving the fan-shaped first and belt-shaped second ultrasonic waves reflected on the inside of the specimen,
wherein the first relational amount is an estimated value of the relationship between two different probe positions on the surface of the specimen, based on the two first ultrasonic images at the two probe positions, wherein the second relational amount results from correcting the first relational amount based on the two second ultrasonic images at the two probe positions; and synthesizing one of the first and second ultrasonic images at one of the two positions on the cross section with the one of the first and second ultrasonic images at the other position based on the second relational amount.

\* \* \* \* \*